US008658573B2

(12) United States Patent
Wang et al.

(10) Patent No.: US 8,658,573 B2
(45) Date of Patent: Feb. 25, 2014

(54) PHOTO-GENERATED CARBOHYDRATE ARRAYS AND THE RAPID IDENTIFICATION OF PATHOGEN-SPECIFIC ANTIGENS AND ANTIBODIES

(75) Inventors: Denong Wang, Palo Alto, CA (US); Gregory T. Carroll, New York, NY (US); Nicholas J. Turro, Tenafly, NJ (US); Jeffrey T. Koberstein, Storrs, CT (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1244 days.

(21) Appl. No.: 11/900,221

(22) Filed: Sep. 11, 2007

(65) Prior Publication Data

US 2010/0331198 A1 Dec. 30, 2010

Related U.S. Application Data

(60) Provisional application No. 60/843,674, filed on Sep. 11, 2006, provisional application No. 60/858,069, filed on Nov. 9, 2006.

(51) Int. Cl.

| | |
|---|---|
| ***C40B 40/12*** | (2006.01) |
| ***C40B 60/12*** | (2006.01) |
| ***C08L 5/00*** | (2006.01) |
| *C40B 20/02* | (2006.01) |
| *C40B 30/04* | (2006.01) |
| *C40B 50/18* | (2006.01) |

(52) U.S. Cl.
USPC .......... 506/19; 506/3; 506/9; 506/32; 506/39; 106/162.1; 106/217.5

(58) Field of Classification Search
None
See application file for complete search history.

(56) References Cited

U.S. PATENT DOCUMENTS

| | | | |
|---|---|---|---|
| 6,080,589 | A | 6/2000 | Kandil et al. |
| 6,329,209 | B1 | 12/2001 | Wagner et al. |
| 6,355,491 | B1 | 3/2002 | Zhou et al. |
| 6,828,110 | B2 | 12/2004 | Lee et al. |

(Continued)

FOREIGN PATENT DOCUMENTS

| | | |
|---|---|---|
| WO | WO-02/064556 | 8/2002 |
| WO | WO-2004/025268 | 3/2004 |

(Continued)

OTHER PUBLICATIONS

Dauberspeck et al., "Novel Oligosaccharide Side Chains of the Collagen-like Region of BclA, the Major Glycoprotein of the *Bacillus anthracis* Exosporium", 2004, JBC, 279(20):30945-53).*

(Continued)

*Primary Examiner* — Christopher M Babic
*Assistant Examiner* — Jeremy C Flinders
(74) *Attorney, Agent, or Firm* — Wilmer Cutler Pickering Hale and Dorr LLP

(57) ABSTRACT

The invention relates to novel photo-generated carbohydrate arrays and methods of their use to detect the presence of one or more agents in a sample. The invention also relates to a high-throughput strategy to facilitate the identification and immunological characterization of pathogen-specific carbohydrates, including those of *Bacillus anthracis*. The invention can be used to determine the presence of a pathogen and whether a subject has been exposed to a pathogen, such as by screening for pathogen-specific antibodies.

22 Claims, 7 Drawing Sheets

(56) References Cited

U.S. PATENT DOCUMENTS

| | | | |
|---|---|---|---|
| 2003/0078314 A1 | 4/2003 | Johnson et al. |
| 2003/0215801 A1 | 11/2003 | Pieken et al. |
| 2003/0228637 A1 | 12/2003 | Wang |
| 2004/0033546 A1 | 2/2004 | Wang |
| 2004/0253634 A1 | 12/2004 | Wang |
| 2005/0032081 A1 | 2/2005 | Ju et al. |
| 2007/0020620 A1 | 1/2007 | Finn et al. |
| 2010/0099580 A1 | 4/2010 | Carroll et al. |

FOREIGN PATENT DOCUMENTS

| | | |
|---|---|---|
| WO | WO-2004/106886 | 12/2004 |
| WO | WO 2005060668 A2 * | 7/2005 |
| WO | WO-2006/064505 | 6/2006 |
| WO | WO-2008/054398 | 5/2008 |

OTHER PUBLICATIONS

Wang et al., "Carbohydrate microarrays for the recognition of cross-reactive molecular markers of microbes and host cells", Nature Biotechnology, 2002, 20:275-281.*

Huang et al., "Prostate-specific antigen immunosensing based on mixed self-assembled monolayers, camel antibodies and colloidal gold enhanced sandwich assays", 2005, Biosensors and Bioelectronics, 21:483-490.*

Liu et al., "Micro-patterning of 3-aminopropyltrimethoxy-silane self-assembled monolayers with colloidal gold", 1998, Supramolecular Science, pp. 705-708.*

Peramo et al., Langmuir, 2006, 22:3228-3234.*

Heid et al. (Langmuir, 1996, 12:2118-2120).*

Adamo, R. et al.,"Synthesis of the β anomer of the spacer-equipped tetrasaccharide side chain of the major glycoprotein of the *Bacillus anthracis* exosporium," *Carbohydrate Research,* 340, 2579-2582 (2005).

Adams, E. W.; et al. "Oligosaccharide and glycoprotein microarrays as tools in HIV glycobiology: Glycan-dependent gp120/protein interactions." *Chemistry & Biology.* 2004, 11(6): 875-881.

Angeloni, S.; et al. "Glycoprofiling with micro-arrays of glycoconjugates and lectins." *Glycobiology.* 2005, 15(1): 31-41.

Blixt, O.; et al. "Printed covalent glycan array for ligand profiling of diverse glycan binding proteins." *Proceedings of the National Academy of Sciences of the United States of America.* 2004, 101(49): 17033-17038.

Boydston, et al., "Orientation within the Exosporium and Structural Stability of the Collagen-Like Glycoprotein BclA of *Bacillus anthracis,*"., J Bacteriol 2005, 187, 5310-5317.

Brun MA, Disney MD, Seeberger PH. Miniaturization of microwave-assisted carbohydrate functionalization to create oligosaccharide microarrays. *ChemBioChem* 2006, 7, 421-424.

Bryan, M.C., Lee, L.V. & Wong, C.-H. High-throughput identification of fucosyltransferase inhibitors using carbohydrate microarrays. *Bioorg. Med. Chem. Lett.* 14, 3185-3188 (2004).

Calarese et al., "Dissection of the carbohydrate specificty of the broadly neutralizing anti-HIV-1 antibody 2G12,"PNAS, vol. 102, pp. 13372-13377 (Sep. 2005).

Carroll, G. T.,et al., "Photochemical micropatterning of Carbohydrates on Surface," *Langmuir* 2006, 22, 2899-2905.

Charych, D. H.; et al. "Direct colorimetric detection of a receptor-ligand interaction by a polymerized bilayer assembly." *Science.* 1993, 261(5121): 585-588.

Charych, D.; et al. "A 'litmus test' for molecular recognition using artificial membranes." Chemistry & Biology. 1996, 3: 113-120.

Chee, M.; et al. "Accessing genetic information with high-density DNA arrays." *Science.* 1996, 274(5287): 610-614.

Choi, "Glycomics researches seach for the elusive sweet spot. Carbohydrate array development continues, but sample variety remains limited," The Scientist, pp. 30-31 (Mar. 28, 2005).

Ciccotosto, S.; et al. "Synthesis and evaluation of N-acetylneuraminic acid-based affinity matrices for the purification of sialic acid-recognizing proteins." *Glycoconjugate Journal.* 1998, 15: 663-669.

Cisar, J.,et al., "Binding properties of immunoglobulin combining sites specific for terminal or nonterminal antigenic determinants in dextran,", J. Exp. Med. 1975, 142, 435-459.

Cohen, S.et al.,Attenuated Nontoxinogenic and Nonencapsulated Recombinant *Bacillus anthracis* Spore Vaccines Protect against Anthrax, Infect Immun 2000, 68, 4549-4558.

Daubenspeck, et al., "Novel Oligosaccharide Side Chains of the Collagen-like Region of BclA, the Major Glycoprotein of the *Bacillus anthracis,*" J Biol Chem 2004, 279, 30945-30953.

De Smet, L.C.P.M. et al. Covalently attached saccharides on silicon surfaces. *J. Am. Chem. Soc.* 125, 13916-13917 (2003).

Devaraj et al., "Chemoselective covalent coupling of oligonucleotide probes to self-assembled monolayers," J.Am Chem Soc., vol. 127, pp. 8600-8601 (Jun. 22, 2005).

Disney, M. D.; and P. H. Seeberger. "The use of carbohydrate microarrays to study carbohydrate-cell interactions and to detect pathogens." *Chemistry & Biology.* 2004, 11(12): 1701-1707.

Fang, Y.; et al. "Ganglioside microarrays for toxin detection." *Langmuir.* 2003, 19: 1500-1505.

Fazio, F.; et al. "Synthesis of sugar arrays in microtiter plate." *Journal of the American Chemical Society.* 2002, 124: 14397-14402.

Feizi, T.; and W. Chai. "Oligosaccharide microarrays to decipher the glyco code." *Nature Reviews.* 2004, 5: 582-588.

Fodor, S. P. A.; et al. "Multiplexed biochemical assays with biological chips " *Nature.* 1993, 364: 555-556.

Fukui, S.; et al. "Oligosaccharide microarrays for high-throughput detection and specificity assignments of carbohydrate-protein interactions." *Nature Biotechnology.* 2002, 20(10): 1011-1017.

Giannasca, K. T.; et al. "Adherence of *Salmonella typhimurium* to Caco-2 cells: Identification of a glycoconjugate receptor." Infection and Immunity. 1996, 64(1): 135-145.

Heidelberger M., "Cross-reactions of glucose-containing polysaccharides in antipneumococcal sera," *J. Immunology;* 91:735-9, (1963).

Heidelberger M.et al., "Cross-reactions of the group-specific polysacchariddes of streptococcal groups B and G in anti-pneumococcal sera with especial references to type XXIII and its determinants," *J. Immunology* 99:794-6, (1967).

Heller et al., "DNA microarray technology: Devices, systems and applications," Annual Reviews in Biomedical Engineering, vol. 4, pp. 129-153 (2005).

Horan, N.; et al. "Nonstatistical binding of a protein to clustered carbohydrates." *Proceedings of the National Academy of Sciences of the United States of America.* 1999, 96(21): 11782-11786.

Houseman, B. T.; and M. Mrksich. "Carbohydrate arrays for the evaluation of protein binding and enzymatic modification." *Chemistry & Biology.* 2002, 9: 443-454.

Houseman, B. T.; et al. "Maleimide-functionalized self-assembled monolayers for the preparation of peptide and carbohydrate biochips." *Langmuir.* 2003, 19(5): 1522-1531.

Iqbal et al., "A review of molecular recognition technologies for detection of biological threat agents," *Biosensors & Bioelectronics,* vol. 15, pp. 549-578 (2000).

Jelinek, R.; and S. Kolusheva. "Carbohydrate biosensors." *Chem. Rev.* 2004, 104: 5987-6015.

Kobayashi, K.; et al. "Glycopeptide derived from hen egg ovomucin has the ability to bind enterohemorrhagic *Escherichia coli* O157:H7." *Journal of Agricultural and Food Chemistry.* 2004, 52(18): 5740-5746.

Kovac, P., Lerner, L., "Systematic Chemical synthesis and N.M.R. spectra of methyl α-Glycosides of isomalto-oligosaccharides and related compounds," Carbohydr Res 1988, 184, 87-112.

Kovác et. al., "Synthesis of Ligands related to the O-Specific antigen of Type 1 Shigella dysenterin. 3. Glycosylation of 4,6-O-Substitute derivatives of Methyl 2-Acetamido-2-deoxy-α-D-glucopyranoside with Glycosyl donors derived from Mono-and Oligosaccharides " *Journal of Organic Chemistry,* 57, 2455-2467 (1992).

Kramer, M. J., Roth, I. L., "Electron microscopie evidence for a double hair-like nap appearing at low frequency on *Bacillus anthracis* Sterne spores," *Can J Microbiol* 1969, 15, 1247-1248.

Kramer, M. J., Roth, I. L., "Ultrastructural differences in the exosporium of the Sterne and Vollum strains of *Bacillus anthracis,"* *Can J Microbiol* 1968, 14, 1297-1299.

(56) References Cited

OTHER PUBLICATIONS

Kuziemko, G. M.; et al. "Cholera Toxin Binding Affinity and Specificity for Gangliosides Determined by Surface Plasmon Resonance," Biochemistry. 1996, 35: 6375-6384.
Lai, et al., Proteomic Analysis of the Spore Coats of *Bacillus subtilis* and *Bacillus anthraces,* J Bacteriol 2003, 185, 1443-1454.
Lee, M.; and I. Shin. "Facile preparation of carbohydrate microarrays by site-specific, covalent immobilization of unmodified carbohydrates on hydrazide-coated glass slides." *Organic Letters.* 2005, 7(19): 4269-4272.
Lee, W.; et al. "Protein array consisting of sol-gel bioactive platform for detection of *E-coli* O157:H7." *Biosensors and Bioelectronics.* 2005, 20(11): 2292-2299.
Lipshutz, R. J.; et al. "High density synthetic oligonucleotide arrays " Nature Genetics. 1999, 21: 20-24.
Liu, G.-Y. & Amro, N.A. Positioning protein molecules on surfaces: a nanoengineering approach to supramolecular chemistry. *Proc. Natl. Acad. Sci. U. S. A.* 99, 5165-5170 (2002).
Love, K. R.; and P. H. Seeberger. "Carbohydrate arrays as tools for glycomics." *Angewandte Chemie International Edition.* 2002, 41(19): 3583-3586.
MacBeath, G.; et al. "Printing small molecules as microarrays and detecting protein-ligand interactions en masse." *Journal of the American Chemistry Society.* 1999, 121: 7967-7968.
Mahal, L. K. "Catching bacteria with sugar." *Chemistry & Biology.* 2004, 11(12): 1602-1604.
Mammen, M.; et al. "Polyvalent interactions in biological systems: Implications for design and use of multivalent ligands and inhibitors." *Angewandte Chemie International Edition.* 1998, 37: 2754-2794.
Mock, M, Fouet A., "Anthrax" Annu Rev Microbiol, vol. 55, pp. 647-671 (2001).
Newcombe, et al., "Survival of Spacecraft-Associated Microorganisms under Simulated Martian UV Irradiation," Appl Environ Microbiol 2005, 71, 8147-8156.
Ngundi, M. M.; et al. "Detection of bacterial toxins with monosaccharide arrays." *Biosensors and Bioelectronics.* 2006, 21(7): 1195-1201.
Ni, J. H.; et al. "Synthesis of maleimide-activated carbohydrates as chemoselective tags for site-specific glycosylation of peptides and proteins." *Bioconjugate Chemistry.* 2003, 14(1): 232-238.
Park, S.; and I. Shin. "Fabrication of carbohydrate chips for studying protein-carbohydrate interactions." *Angewandte Chemie International Edition.* 2002, 41: 3180-3182.
Park, S.; et al. "Carbohydrate chips for studying high-throughput carbohydrate-protein interactions." *Journal of the American Chemical Society.* 2004, 126(15): 4812-4819.
Pavliak et. al., "Stereoselective syntheses of a di-,tri-, and tetra-saccharide fragment of *Shigella dysenteriae* typr 1 O-antigen using 3,4,6-tri-O-acetyl-2-azido-2-deoxy-α-D-glucopyranosyl chloride as a glycosyl donor," *Carbohydrate Research,* 229, 103-116 (1992).
Pope, M. R.; et al. "Specific activity of polypyrrole nanoparticulate immunoreagents: Comparison of surface chemistry and immobilization options." *Bioconjugate Chemistry.* 1996, 7: 436-444.
Puu, G. "An approach for analysis of protein toxins based on thin films of lipid mixtures in an optical biosensor." *Analytical Chemistry.* 2001, 73: 72-79.
Ratner, D. M.; et al. "Probing protein-carbohydrate interactions with microarrays of synthetic oligosaccharides." *ChemBioChem.* 2004, 5: 379-382.
Ratner, D. M.; et al. "Tools for glycomics: Mapping interactions of carbohydrates in biological systems." *ChemBioChem.* 2004, 5(10): 1375-1383.
Redmond,et al., "Identification of proteins in the exosporium of *Bacillus anthraces,", Microbiology* 2004, 150, 355-363.
Resnick, "New Glycan arrays discover autoimmunogenic activities of SARS-CoV: concern over monkey vaccine," Medical New Today, Article URL: http://www.medicalnewstoday.com/releases/11474.php, 4 pages (Jul. 31, 2004).
Rezania, A.; et al."Bioactivation of metal oxide surfaces. 1. Surface characterization and cell response." *Langmuir.* 1999, 15: 6931-6939.
Rowe Taitt, C; et al. "Evanescent wave fluorescence biosensors." *Biosensors and Bioelectronics.* 2005, 20(12): 2470-2487.
Rowe-Taitt, C. A.; et al. "A ganglioside-based assay for cholera toxin using an array biosensor." *Analytical Biochemistry.* 2000, 281(1): 123-133.
Rowe-Taitt, C. A.; et al. "Array biosensor for detection of biohazards." *Biosensors and Bioelectronics.* 2000, 14(10-11): 785-794.
Rowe-Taitt, C. A.; et al. "Simultaneous detection of six biohazardous agents using a planar waveguide array biosensor." *Biosensors and Bioelectronics.* 2000, 15(11-12): 579-589.
Roy, A. & Roy, N., "Structure of the capsular polysaccharide from *Streptococcus pneumoniae," Carbohydrate Research,* 126:271-7, (1984).
Saksena et. al., "one-pot preparation of a series of glycoconjugates with predetermined antigen-carrier ratio from oligosaccharides that mimic the O-ps of vibrio cholerae O:1, serotype Ogawa," *Carbohydrate Research,* 338, 2591-2603 (2003).
Saksena, R. et al., "Studies toward a conjugate vaccine for anthrax. Synthesis and characterization of anthrsoe [4,6-dideoxy-4-(3-hydroxy-3-methylbutanamido)-2-O-methyl-D-glucopyranose] and its methyl glycosides," *Carbohydrate Research,* 340, 1591-1600 (2005).
Saksena, R. et al., "Synthesis of the tetrasaccharide side chain of the major glycoprotein of the *Bacillus anthracis* exosporium," *Bioorganic and Medicinal Chemistry Letters,* 16, 615-617.
Sapsford, K. E.; et al. "Detection of *Campylobacter* and *Shigella* species in food samples using an array biosensor." *Analytical Chemistry.* 2004, 76: 433-440.
Schmidt,"Sugar rush," New Scientist , vol. 176, issue 2366, pp. 34 (Oct. 2002).
Seeberger, P. H.; and M. D. Disney. "Carbohydrate microarrays as versatile tools for glycobiology." *Glycobiology.* 2004, 14(11): 1073-1073.
Seo et al., "Photocleavable fluorescent nucleotides for DNA sequencing on a chip constructed by site-specific coupling chemistry," *PNAS USA,* vol. 101, pp. 5488-93 (Apr. 13, 2004).
Shin, I. J.; et al. "Carbohydrate arrays for functional studies of carbohydrates." *Combinatorial Chemistry & High Throughput Screening.* 2004, 7(6): 565-574.
Shin, I.; et al. "Carbohydrate microarrays: An advanced technology for functional studies of glycans." *Chemistry-a European Journal.* 2005, 11(10): 2894-2901.
Song, X.; et al. "Direct, ultrasensitive, and selective optical detection of protein toxins using multivalent interactions." *Analytical Chemistry.* 1999, 71: 2097-2107.
Song, X.; et al. "Flow cytometry-based biosensor for detection of multivalent proteins." *Analytical Biochemistry.* 2000, 284: 35-41.
Steichen, et al., "Identification of the Immunodominant Protein and Other Proteins of the *Bacillus anthracis* Exosporium," *J Bacteriol* 2003, 185, 1903-1910.
Sun et al., "Carbohydrate and protein immobilization onto solid surfaces by sequential Diels-Alder and azide-alkyne cycloadditions," Bioconjug Chem, vol. 17, pp. 52-57 (Jan.-Feb. 2006).
Sylvestre, et al., "A Collagen-like surface glycoprotein is a structural component on the *Bacillus anthracis* exosporium," *Mol Microbiol* 2002, 45, 169-178.
Tamborrini et al., "Anti-Carbohydrate antibodies for the detection of anthrax spores," Angew. Chem Int. Ed., vol. 45, pp. 1-3 (2006).
Tamborrini, et al., "Anti-Carbohydrate Antibodies for the Detection of Anthrax Spores." *Angewandte Chemie International Edition.* vol. 45, Issue 39 , pp. 6581-6582. Published Online: Aug. 17, 2006.
Tang, P. W.; and T. Feizi. "Neoglycolipid micro-immunoassays applied to the oligosaccharides of human-milk galactosyltransferase detect blood-group related antigens on both o-linked and n-linked chains." *Carbohydrate Research.* 1987, 161(1): 133-143.
Tang, P. W.; et al. "Novel approach to the study of the antigenicities and receptor functions of carbohydrate chains of glycoproteins." *Biochemical and Biophysical Research Communications.* 1985, 132(2): 474-480.

(56) References Cited

OTHER PUBLICATIONS

Turnbull, P. C. B., Current status of immunization against anthrax: old vaccines may be here to stay for a while, Curr. Opin. Infect. Dis. 2000, 13, 113-120.
Wadkins, R. M.; et al. "Detection of multiple toxic agents using a planar array immunosensor." *Biosensors and Bioelectronics.* 1998, 13(3-4): 407-415.
Wang D. Carbohydrate antigens. In: *Encyclopedia of Molecular Cell Biology and Molecular Medicine,* edited by Meyers RA. Wiley-VCH, 2004, vol. II, chapt. 11, p. 277-301.
Wang et al., "A Carbohydrate-based microarray system for characterizing AIDS-associated microbial infections," Preliminary Program, AIDS Vaccine 2001-Sep. 5-8, 2001, Philadelphia, 1 page.
Wang et al., "Photogenerated Glycan arrays identify immunogenic sugar moieties of *Bacillus anthracis* exosporium," Proteomics, vol. 7, pp. 180-184 (2007).
Wang, D. "Carbohydrate microarrays for the recognition of cross-reactive molecular markers of microbes and host cells." *Nature Biotechnology.* 2002, 20: 275-281.
Wang, D., "Carbohydrate microarrays," *Proteomics* 2003, 3, 2167-2175.
Wang, D., et al. "Glycan arrays lead to the discovery of autoimmunogenic activity of SARS-CoV," *Physiol Genomics* 2004, 18, 245-248.
Wang, R.,et al., "A Practical Protocol for Carbohydrate Microarrays," *Methods Mol Biol* 2005, 310, 241-252.
Wang, S. P.;et al., "Immunologic relationship between genital TRIC, lymphogranuloma venereum, and related organisms in a new microtiter indirect immunofluorescence test," American Journal of Ophthalmology. 1970, 70(3): 367-374.
Webb, G. F., "A silent bomb: The risk of anthrax as a weapon of mass destruction," Proc Natl Acad Sci U S A 2003, 100, 4355-4356.
Willats William, G.T., Rasmussen Svend, E., Kristensen, T., Mikkelsen Jorn, D. & Knox, J.P. Sugar-coated microarrays: a novel slide surface for the high-throughput analysis of glycans. *Proteomics* 2, 1666-1671 (2002).
Williams,et al., "Species-Specific Peptide Ligands for the Detection of *Bacillus anthracis* Spores,", Appl Environ Microbiol 2003, 69, 6288-6293.
Xiao, S. J.; et al. "Immobilization of the cell-adhesive peptide Arg-Gly-Asp-Cys (RGDC) on titanium surfaces by covalent chemical attachment." *Journal of Materials Science: Materials in Medicine.* 1997, 8: 867-872.
Xiao, S.-J.; et al. "Covalent attachment of cell-adhesive, (Arg-Gly-Asp)-containing peptides to titanium surfaces." *Langmuir.* 1998, 14: 5507-5516.
Zhang et al., "Carbohydrate-Protein Interactions by "Clicked" Carbohydrate Self-Assembled Monolayers," Annal. Chem., vol. 78, pp. 2001-2008 (Mar. 15, 2006).
Zhang, J. & Kovac, P., "Synthesis of methyl α-glycosides of some higher oligosaccharide fragments of the O-antigen of Vibrio Cholerae O1, serotype Inaba and Ogawa " *Carbohydrate Research,* 300, 329-339 (1997).
Zhang, Y.; et al. "Studying the interaction of α-Gal carbohydrate antigen and proteins by quartz-crystal microbalance." *Journal of the American Chemical Society.* 2003, 125: 9292-9293.
Zhou et al., "Oligosaccharide microarrays fabricated on aminooxyacetyl functionalized glass surface for characteization of carbohydrate-protein interaction," Biosens Bioelecton, vol. 21, pp. 1451-8 (Feb. 2006).
Zhou et al., "Oligosaccharide microarrays fabricated on aminooxyacetyl functionalized glass surface for characteization of carbohydrate-protein interaction," Biosens Bioelecton, vol. 21, pp. 1-8 (2005).
Carroll et al., "Photo-Generation of Carbohydrate MicroArrays," in Microarrays, Preparation, Microfluidics, Detection Methods, and Biological Applications, Dill, K. et al, Eds., Springer New York, Ch. 9, pp. 191-210 (2009).

* cited by examiner

Location of carbohydrates

| | A | B | C |
|---|---|---|---|
| 1 | Isolichen | **Anthrose-β Tri.** | **Anthrose-β Tetra.** |
| 2 | α-L-RhaGal | 5-Me-α-L-Rha | 5-Me-β-Rha Tri. |
| 3 | α-L-RhaRha | 5-Me-α-RhaRha | 5-Me-a-Rha Tri. |
| 4 | α-L-Rha-RhaGal | **Anthrose-α Tetra** | Anthrose-β |
| 5 | α-D-GlcNAc Pento | 5-Me-β-L-Rha | Pn23 |

Figure 2B

PHOTO-GENERATED CARBOHYDRATE ARRAYS AND THE RAPID IDENTIFICATION OF PATHOGEN-SPECIFIC ANTIGENS AND ANTIBODIES

This application claims priority to U.S. Provisional Application Nos. 60/858,069, filed Nov. 9, 2006, and 60/843,674, filed Sep. 11, 2006, each of which are hereby incorporated by reference in their entirety.

The work described herein was supported in whole, or in part, by National Institute of Health Grant No. AI064104; U.S. Army Research Laboratory and the U.S. Army Research Office Grant No. DA W911NF-04-1-0282 and the National Science Foundation Grant Nos. DMR-02-14263, IGERT-02-21589 and CHE-04-15516. Thus, the United States Government has certain rights to the invention.

All patents, patent applications and publications cited herein are hereby incorporated by reference in their entirety.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Diseases must be diagnosed quickly in order to maximize the chances for their successful medical treatment and containment. One method of diagnosis employs biomarkers linked to specific diseases. The efficient identification of biomarkers for specific diseases will greatly facilitate quick diagnoses, the discovery of new biomarkers, and the development of new vaccines.

The alarming rate of appearance of drug resistant diseases underscores the need to expand our methods to treat diseases, including by vaccines. However, it is often difficult to determine or predict the effectiveness of a vaccine. A quick and efficient means to determine the ability of a vaccine to stimulate an immune response would greatly facilitate the search for novel vaccines.

Another pressing concern is the threat of bioterror attacks such as with anthrax. Anthrax is an often-fatal infectious disease caused by the bacterium *Bacillus anthracis* (*B. anthracis*), which begins by the entry of spores into the mammalian host. To combat the use of *B. anthracis* spores as a biological weapon, a rapid and specific method to detect *B. anthracis* spores is needed. In addition, the serious side effects accompanying currently used anthrax vaccines emphasize the need to find a safer anthrax vaccine.

Cell-surface carbohydrates show promise as biomarkers to study immune responses. Yet carbohydrates have not been efficiently harnessed as biomarkers for disease detection, biomarker identification, or vaccine development.

SUMMARY OF THE INVENTION

In one embodiment, the invention relates to an array that includes:

a surface;

a compound of formula (I):

(I)

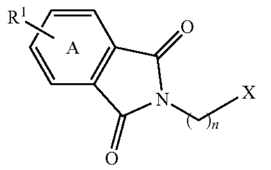

immobilized on at least a part of the surface; and one or more carbohydrates attached to the surface through a covalent bond to the compound of formula (I);

wherein one or more of the carbohydrates are capable of binding to an agent, wherein the agent is capable of indicating a presence of a disease or a pathogen;

n is an integer from 1 to 100;

X is $R^2$, —$CO_2R^3$, —$C(O)NR^3R^3$, —$SR^4$, —CN, —$OR^3$, a halogen, a β-diketone, a silane, a phosphate, a phosphonate, a polymer, or block copolymer;

ring A is substituted with one or more $R_1$ groups;

$R_1$ is independently a halogen, a hydroxyl, an aryl, an amide, a cyano, a nitro, —$R^2$, —$C(O)R^3$, —$CO_2R^3$, —$OC(O)R^3$, or —$OR^3$, $R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —$OC(O)R^5$;

$R^3$ is independently a hydrogen, a substituted or unsubstituted $C_1$-$C_{10}$ straight-chain or branched-chain alkyl, or a substituted or unsubstituted alkene which contains 2-4 carbons;

$R^4$ is independently a hydrogen, —S-pyridyl, —$SR^3$, —$SO_2R^3$, or $SR^8$, wherein —$SR^8$ and the rest of formula (I) combine to form a bis-disulfide; and $R^5$ is independently a hydrogen, an unsubstituted straight- or branched-chain alkyl that contains 1-6 carbons, or a straight- or branched-chain alkyl that contains 1-6 carbons and is substituted by an alkyne.

In one embodiment, the invention relates to a method for determining the presence of a pathogen or for diagnosing a disease in a subject, where the method includes:

exposing an array as described herein to a sample from a subject; and determining the presence of the agent bound to one or more of the carbohydrates, wherein the presence of a bound agent indicates the presence of a pathogen in the sample.

In another embodiment, the invention relates to an array that includes:

a surface;

a compound of Formula (I) immobilized on the surface:

(I)

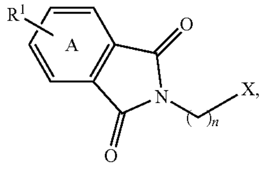

a compound of Formula (III) immobilized on the surface:

(III)

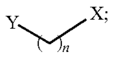

one or more carbohydrates attached to the surface through a covalent bond to the compound of formula (I), wherein:

one or more of the carbohydrates are capable of binding to an agent, wherein the agent is capable of indicating a presence of a disease or a pathogen;

n is an integer from 1 to 100;

X is $R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer;

ring A is substituted with one or more $R_1$ groups;

$R_1$ is independently a halogen, a hydroxyl, an aryl, an amide, a cyano, a nitro, —$R^2$, —C(O)$R^3$, —$CO_2R^3$, —OC(O)$R^3$, or —$OR^3$;

$R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$;

$R^3$ is independently a hydrogen, a substituted or unsubstituted $C_1$-$C_{10}$ straight-chain or branched-chain alkyl, or a substituted or unsubstituted alkene which contains 2-4 carbons;

$R^4$ is independently a hydrogen, —S-pyridyl, —$SR^3$, —$SO_2R^3$, or $SR^8$, wherein —$SR^8$ and the rest of formula (I) combine to form a bis-disulfide;

$R^5$ is independently a hydrogen, an unsubstituted straight- or branched-chain alkyl that contains 1-6 carbons, or a straight- or branched-chain alkyl that contains 1-6 carbons and is substituted by an alkyne; and Y is —$NR^3R^3$, —OH, —SH, —C(O)$NR^3R^3$, —$CO_2H$, an ammonium, or a salt thereof.

In one embodiment, the invention relates to a method for making an array, where the method includes:

forming on at least a part of a surface a self-assembled monolayer comprising a compound of formula (I):

(I)

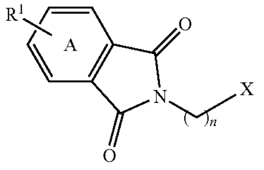

depositing one or more carbohydrates onto at least a part of the monolayer; and irradiating the carbohydrate, monolayer, and optionally the surface, wherein:

a covalent bond is formed between the carbohydrate and the compound of formula (I);

the carbohydrate is capable of binding to an agent, wherein the agent is capable of indicating a presence of a disease or a pathogen;

n is an integer from 1 to 100;

X is $R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer;

ring A is substituted with one or more $R_1$ groups;

$R_1$ is independently a halogen, a hydroxyl, an aryl, an amide, a cyano, a nitro, —$R^2$, —C(O)$R^3$, —$CO_2R^3$, —OC(O)$R^3$, or —$OR^3$;

$R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$;

$R^3$ is independently a hydrogen, a substituted or unsubstituted $C_1$-$C_{10}$ straight-chain or branched-chain alkyl, or a substituted or unsubstituted alkene which contains 2-4 carbons;

$R^4$ is independently a hydrogen, —S-pyridyl, —$SR^3$, —$SO_2R^3$, or $SR^8$, wherein —$SR^8$ and the rest of formula (I) combine to form a bis-disulfide; and $R^5$ is independently a hydrogen, an unsubstituted straight- or branched-chain alkyl that contains 1-6 carbons, or a straight- or branched-chain alkyl that contains 1-6 carbons and is substituted by an alkyne.

In one embodiment, the invention relates to a method for making an array, where the method includes:

forming on at least a part of a surface a self-assembled monolayer, wherein the monolayer comprises a compound of Formula (I)

(I)

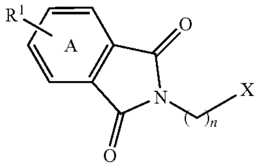

and a compound of Formula (III)

(III)

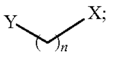

depositing at least one carbohydrate onto at least a part of the monolayer; and irradiating the carbohydrate, monolayer, and optionally the surface, wherein:

a covalent bond is formed between the carbohydrate and the compound of formula (I);

the carbohydrate is capable of binding to an agent, wherein the agent is capable of indicating a presence of a disease or a pathogen;

n is an integer from 1 to 100;

X is $R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer;

ring A is substituted with one or more $R_1$ groups;

$R_1$ is independently a halogen, a hydroxyl, an aryl, an amide, a cyano, a nitro, —$R^2$, —C(O)$R^3$, —$CO_2R^3$, —OC(O)$R^3$, or —$OR^3$;

$R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$;

$R^3$ is independently a hydrogen, a substituted or unsubstituted $C_1$-$C_{10}$ straight-chain or branched-chain alkyl, or a substituted or unsubstituted alkene which contains 2-4 carbons;

$R^4$ is independently a hydrogen, —S-pyridyl, —$SR^3$, —$SO_2R^3$, or $SR^8$, wherein —$SR^8$ and the rest of formula (I) combine to form a bis-disulfide;

$R^5$ is independently a hydrogen, an unsubstituted straight- or branched-chain alkyl that contains 1-6 carbons, or a straight- or branched-chain alkyl that contains 1-6 carbons and is substituted by an alkyne; and Y is —$NR^3R^3$, —OH, —SH, —$C(O)NR^3R^3$, —$CO_2H$, an ammonium, or a salt thereof.

In one embodiment, the invention relates to a method for detecting a molecule that inhibits an agent-carbohydrate interaction, where the method includes:

depositing an agent onto a carbohydrate on an array;

washing the structure to substantially remove any unbound agent;

incubating the bound agent with a molecule, wherein the molecule is capable of binding to the agent and displacing the first carbohydrate;

incubating the array with an anti-agent antibody;

washing the structure to substantially remove any unbound anti-agent antibody;

treating the array with a labeled secondary antibody;

reading the array with a label reader to determine an amount of bound labeled secondary antibody, wherein a non-zero amount of bound labeled secondary antibody indicates that the molecule inhibits agent-carbohydrate interactions; and wherein the array comprises:

a surface;

a compound of formula (I):

(I)

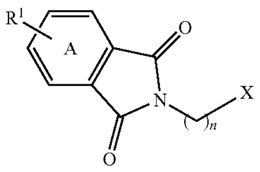

immobilized on at least a part of the surface; and one or more carbohydrates covalently attached to the compound of formula (I); and wherein one or more of the carbohydrates are capable of binding to an agent;

n is an integer from 1 to 100;

X is $R^2$, —$CO_2R^3$, —$C(O)NR^3R^3$, —$SR^4$, —CN, —$OR^3$, a halogen, a β-diketone, a silane, a phosphate, a phosphonate, a polymer, or block copolymer;

ring A is substituted with one or more $R_1$ groups;

$R_1$ is independently a halogen, a hydroxyl, an aryl, an amide, a cyano, a nitro, —$R^2$, —$C(O)R^3$, —$CO_2R^3$, —$OC(O)R^3$, or —$OR^3$;

$R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —$OC(O)R^5$;

$R^3$ is independently a hydrogen, a substituted or unsubstituted $C_1$-$C_{10}$ straight-chain or branched-chain alkyl, or a substituted or unsubstituted alkene which contains 2-4 carbons;

$R^4$ is independently a hydrogen, —S-pyridyl, —$SR^3$, —$SO_2R^3$, or $SR^8$, wherein —$SR^8$ and the rest of formula (I) combine to form a bis-disulfide; and $R^5$ is independently a hydrogen, an unsubstituted straight- or branched-chain alkyl that contains 1-6 carbons, or a straight- or branched-chain alkyl that contains 1-6 carbons and is substituted by an alkyne.

BRIEF DESCRIPTION OF THE FIGURES

FIG. 2B is an expansion of the legend to FIG. 2A.

DETAILED DESCRIPTION OF THE INVENTION

For the purposes of promoting an understanding of the principles of the invention, reference will now be made to specific embodiments. It will nevertheless be understood that no limitation of the scope of the invention is thereby intended. Alteration and further modifications of the invention, and further applications of the principles of the invention as illustrated herein, as would normally occur to one skilled in the art to which the invention relates, are also within the scope of the invention.

DEFINITIONS

As used herein, the term "subject" includes a plant or an animal, such as a mammal, including a human.

As used herein, the term "agent" includes molecules, such as biomarkers and proteins. The term also includes antibodies.

As used herein, the term "monolayer" includes monolayers and multilayers.

Molecules

The invention provides compounds of formula (I):

(I)

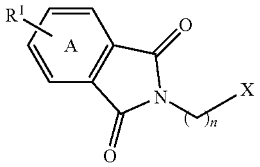

immobilized on at least a part of the surface; and at least one carbohydrate covalently attached to the compound of formula (I);

wherein:

the agent is capable of binding to the carbohydrate;

n is an integer from 1 to 1000, such as 1 to 100, 1 to 30, 1 to 20, 1 to 15, 1 to 10, 5 to 20, 5 to 15, 5 to 10, or 15 to 30, or n is 8, 9, 10, 11, 12, or 13;

X is $R^2$, $—CO_2R^3$, $—C(O)NR^3R^3$, $—SR^4$, —CN, $—OR^3$, a halogen, a β-diketone, a silane, a phosphate, a phosphonate, a polymer, or block copolymer;

ring A is substituted with one or more $R_1$ groups;

each $R_1$ is independently a hydrogen, a halogen, a hydroxyl, an aryl, an amide, a cyano, $—R^2$, $—C(O)R^3$, $—CO_2R^3$, $—OC(O)R^3$, $—OR^3$.

each $R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or $—OC(O)R^5$;

each $R^3$ is independently a hydrogen, a substituted or unsubstituted $C_1$-$C_{10}$ straight-chain or branched-chain alkyl, or a substituted or unsubstituted alkene;

each $R^4$ is independently a hydrogen, —S-pyridyl, $—SR^3$, $—SO_2R^3$, or $SR^8$, where the $—SR^8$ and the rest of formula (I) combine to form a bis-disulfide; and each $R^5$ is independently a hydrogen, an unsubstituted straight- or branched-chain alkyl that contains 1-6 carbons, or a straight- or branched-chain alkyl that contains 1-6 carbons and is substituted by an alkyne.

Examples of compounds of formula (I) are:

I-1

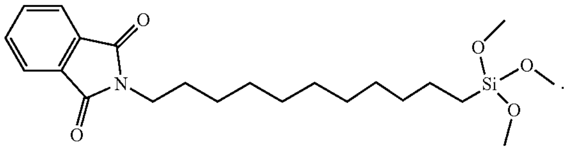

I-2

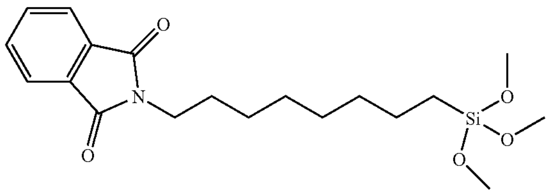

I-3

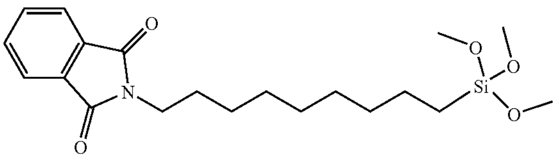

-continued

I-4

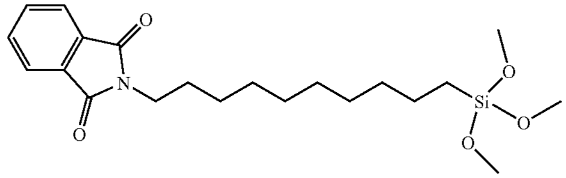

I-5

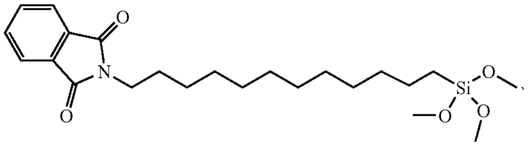

and

I-6

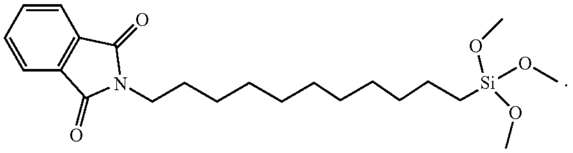

The invention also provides compounds of formula (II):

(II)

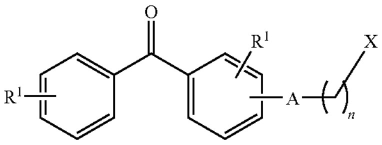

wherein X, $R^1$, and n are as defined above for formula (I); and A is -, $—CH_2$, —C(O)—, —OC(O)—, —C(O)O—, $—C(O)NR^3—$, or $—NR^3C(O)—$.

Examples of Formula (II) are:

II-1

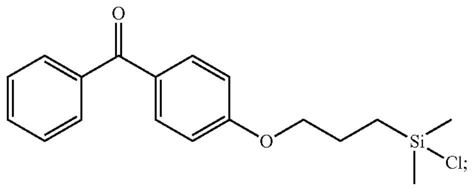

II-2

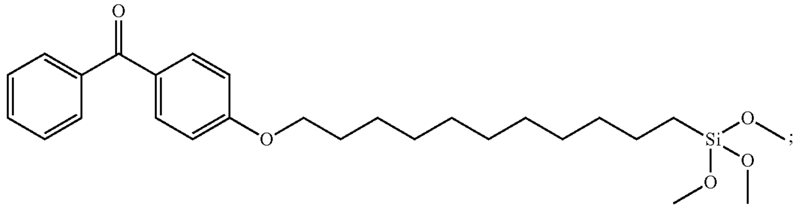

and

-continued

II-3

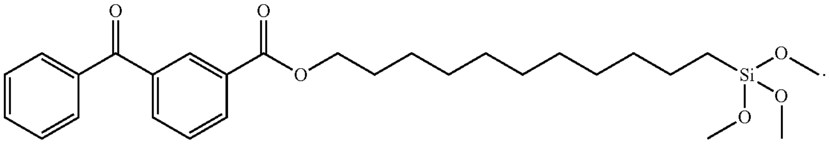

Figure 4:
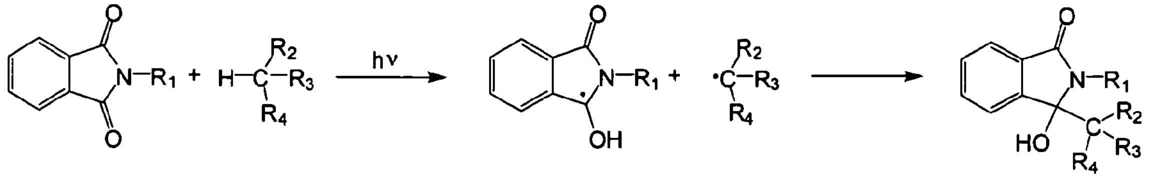
FIG. 4 schematically demonstrates a covalent bond formation from a photochemically-generated phthalimide radical.

In some embodiments, the invention provides photoactive compounds that can form radicals, which lead to the formation of covalent bonds. For example, exposure to UV light can allow a photoactive compound to undergo a radical-based hydrogen abstraction reaction (e.g., abstracting a hydrogen atom from a nearby molecule, such as in. FIG. 4). The resulting radicals can combine, forming a covalent bond. In some embodiments, the photoactive compounds of the invention can include compounds that can form radicals at a carbonyl group. Moreover, the photoactive compounds of the invention can include aryl groups that contain one or more carbonyls that, upon absorption of a photon, can react with hydrogen atom donors (e.g., C—H bonds, Si—H bonds, S—H bonds, and the like) and form covalent bonds. As an example, FIG. 4 schematically demonstrates the abstraction of hydrogen by a phthalimide derivative, which undergoes a transition upon exposure to light to produce an excited state and a radical. As shown, a radical can be generated at a carbonyl group, which then can form a new covalent bond by reacting with nearby molecules. Photoactive compounds that may be used in the present invention include benzophenone and phthalimide derivatives, including individual benzophenone- and phthalimide-containing molecules. Other useful photoactive compounds may be selected based on their ability to become reactive, such as by radical formation, upon irradiation. Other factors that may be considered in selecting such compounds include the compound's excitation wavelength, the presence of other chromophores in the array, and the chemical stability of the compound.

In other embodiments, the nature of the compounds of the invention preclude the need for protecting groups on either the molecules to be attached or the photoactive compounds, which facilitates the generation of the array and the syntheses of the compounds. Additional reagents may not be needed as the radicals form upon irradiation, and then readily form covalent bonds with nearby molecules, such as carbohydrates.

The invention also provides compounds of Formula (III):

(III)

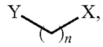

wherein X can be —$R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer; Y can be —$NR^3R^3$, —OH, —SH, —C(O)$NR^3R^3$, —$CO_2$H, a carboxylate, an ammonium, or a salt thereof; and n can be an integer from 1 to 1000, such as 1 to 100, 1 to 30, 1 to 20, 1 to 15, 1 to 10, 5 to 20, 5 to 15, 5 to 10, or 15 to 30, or n is 8, 9, 10, 11, 12, or 13. Each $R^2$ can independently be hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$, wherein $R^5$ can independently be a hydrogen, an unsubstituted straight- or branched-chain alkyl which contains 1-6 carbons, or a straight- or branched-chain alkyl which contains 1-6 carbons and is substituted by an alkyne. Each $R^3$ can independently be a hydrogen, a substituted or unsubstituted $C_1$-$C_{10}$ straight-chain or branched-chain alkyl, or a substituted or unsubstituted alkene. Each $R^4$ can independently be a hydrogen, —S-pyridyl, —$SR^3$, —$SO_2R^3$, or $SR^8$, where the —$SR^8$ and the rest of formula (III) can combine to form a bis-disulfide. In one embodiment, Y is a polar group or a group that has a charge, such as a positive or negative charge. Examples of a compound of formula (III) include those compounds shown below and derivatives thereof:

III-1

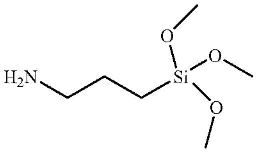

III-2

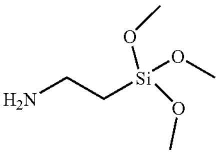

III-3

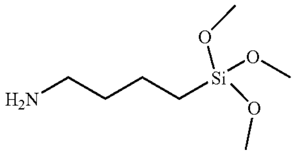

III-4

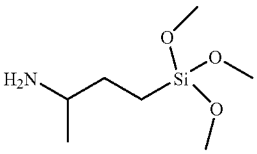

III-5

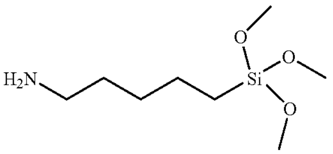

, and

III-6

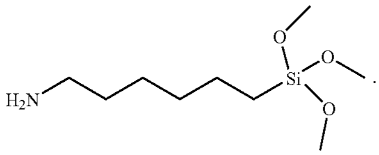

In some embodiments, one or more compounds of Formula (I), (II), and (III), or any combination thereof, can be immobilized on a surface. The compound of Formula (III) can be mixed together with a compound of Formula (I) or (II), or both, prior to or concurrently with addition to the surface. The compound of Formula (III) improves the biomolecular compatibility and/or binding affinity for molecules to be immobilized, such as a carbohydrate, relative to the surface coated with compounds of Formula (I) or (II).

In some embodiments, the ratio of compound of Formula (III) to compound of Formula (I) and/or (II) may be from about 100:1 to about 1:1. For example, the ratio of compound of Formula (III) to compound of Formula (I) and/or (II) may be 80:1, 60:1, 50:1, 30:1, 20:1, 10:1, 5:1, 2:1, and the like.

It is to be appreciated that other photoactive groups may replace the phthalimide or benzophenone of Formula (I) or (II), respectively. Such photoactive groups may include other aromatic or non-aromatic ketone-containing groups, such as xanthones, acetone-type ketones, or derivatives thereof.

Immobilization

In one embodiment, the invention provides a method of immobilizing molecules, such as carbohydrates, on a surface. The method includes forming a self-assembled monolayer on a surface of a substrate, where the self-assembled monolayer includes a compound capable of forming covalent bonds with nearby molecules after irradiation, such as a molecule of Formula I or II, optionally in further combination with a molecule of Formula III; applying carbohydrates on the self-assembled monolayer; and irradiating the system. A photochemical reaction between compounds in the self-assembled monolayer and the carbohydrate results in covalent links between the carbohydrates and the monolayer, immobilizing the carbohydrates at the surface. In some embodiments, the irradiation of the compound may be through a photomask, resulting in a patterned array of carbohydrates. In other embodiments, the carbohydrates may be spotted by hand or using an automated or robotic spotter, such as disclosed in the examples, below. The amount of compound added will depend on the desired amount for each application, as can be readily determined by one skilled in the art. For example, the photoactive compound or mixture thereof, can be in a 0.01% to 10% molar solution, a 0.5% to 5% solution, or a 1% solution.

Other embodiments of the invention also relate to methods for immobilizing molecules on a surface. The methods may generate an array, such as a microarray. Methods of the invention include immobilizing on a surface a photoactive compound capable of forming covalent bonds with nearby molecules after irradiation; applying a molecule to the photoactive compound, the array, the surface, or any combination thereof; and irradiating the photoactive compound, the array, the surface, or any combination thereof, wherein a photochemical reaction between the photoactive compound and the molecule results in covalent links between the molecule and the photoactive compound, which can immobilize the molecule near or on the surface. In certain embodiments, the photoactive compound is immobilized on the surface as a self-assembled monolayer, or a self-assembled mixed-monolayer, or a multilayer (for example, see FIG. 1). In one embodiment, the surface is on a substrate or includes a substrate.

In another embodiment of the invention, the compound capable of forming covalent bonds with nearby molecules after irradiation may be a compound of formula (I), such as a phthalimide or a derivative thereof, a compound of formula (II), such as a mono-benzophenone or a derivative thereof. In some embodiments, the compound may be added to a surface or substrate by spin-coating, or by dissolution in an appropriate organic or aqueous solvent, such as toluene, and addition of the solution to a substrate or surface.

Substrates suitable for the invention include inorganic substrates and organic substrates. In some embodiments, the substrate may be a silicon wafer, glass slide, or polymer slide, or may be made of silica, glass, quartz, silicon, titanium, titania, gold, carbon, alumina, titania, tantalum oxide, germanium, silicon nitride, zeolites, gallium arsenide, gold, platinum, aluminum, copper, titanium, polyacrylamide, nylon, polyethylene, polypropylene, PTFE, PVDF polycarbonate, polystyrene, poly(tert-butyl acrylate), poly(vinyl alcohol), nitrocellulose, polymethylmethacrylate, polyvinylethylene, polyethyleneimine, poly(ethylether)ketone, polyoxymethylene (POM), polyvinylphenol, polylactides, polymethacrylimide (PMI), polyalkenesulfone (PAS), polypropylethylene, polyhydroxyethylmethacrylate (HEMA), polydimethylsiloxane, polyacrylamide, polyimide, or block-copolymers thereof. In an embodiment the substrate may comprise a surface on a sensor. The array of the invention may include or be part of a chip, a plate, a sensor, a slide, or a combination thereof.

In one embodiment, irradiation may be accomplished with light. In more specific embodiments, ultraviolet (UV) light can be used. In other embodiments, light of wavelengths from about 280 to about 400 nm, such as from about 290 to about 305 nm, about 305 to about 315 nm, about 315 to about 350 nm, or about 300 nm, can be used in the invention.

In another embodiment, the carbohydrate may be a monosaccharide, an oligosaccharide, or a polysaccharide. In yet another embodiment, the self-assembled monolayer may comprise a compound of formula (I), such as a mono-phthalimide, a compound of formula (II), such as a mono-benzophenone, or a derivative thereof, optionally in combination with a compound of formula (III).

In some embodiments, methods of the invention include immobilizing on a surface a composition that includes a photoactive compound capable of forming covalent bonds with nearby molecules after irradiation and a second compound that increases the affinity of the nearby molecules for the composition; applying a molecule to the composition; and irradiating the composition, where a photochemical reaction occurs between the photoactive compound and the molecule, resulting in covalent links between the molecule and the photoactive compound and immobilizing the molecule on or near the surface. In certain embodiments, the composition can be immobilized on the surface as a self-assembled monolayer. The second compound may include a polar or charged group, which can be presented at the air-monolayer interface. In a specific embodiment, the group may be an amine or ammonium, or a carboxylic acid or carboxylate. In a more specific embodiment, the second compound is attached to the surface and terminates in a polar group at the end that is not attached to the surface. The photoactive compound and the second compound may be attached to the surface through the same or similar means.

In a specific embodiment, the invention provides a mixed monolayer including a photoactive compound and a second compound capable of increasing the affinity of a nearby molecule for the monolayer comprising the photoactive compound. The second compound may have a polar group, such as an amine. The second compound may be of Formula (III), and the ratio of the second compound to the photoactive compound, such as a compound of Formula (I) or (II), may be from about 1:1 to about 100:1, about 2:1 to about 50:1, about 1:1 to about 25:1, about 2:1 to about 25:1, about 5:1 to about 20:1, about 26:1 to about 50:1, or about 51:1 to about 100:1.

In one embodiment, a self-assembled monolayer containing phthalimide chromophores is capable of photochemically immobilizing carbohydrates on a flat surface. An illustrative method requires no chemical modification of the carbohydrates prior to deposition. Further, because covalent attachment is involved, carbohydrates of all molecular weights can be immobilized. The photochemical nature of the technique allows simple arrays to be created with or without a robot and makes the method adaptable to photolithography. In some embodiments, multiple carbohydrate patterns can be immobilized by repeating the photochemical reaction with a different carbohydrate in a previously masked region, or spotting carbohydrates in alternate, known locations. In conjunction with a microarray spotter, large libraries of carbohydrates may be immobilized on a surface. The versatility and ease of the method provides an opportunity for biologists, chemists and engineers to investigate biological phenomena and create new biological materials.

In one embodiment, the term "array" as used herein includes a microarray.

Compounds of Formula (I) or (II) can also abstract electrons from suitable donors such as amines, sulfides, AIBN, and the like. Electron transfer to the photoactive compound may be followed by proton transfer and covalent bond formation in a manner similar to the radical hydrogen abstraction in FIG. 4.

In some embodiments, the photoactive compound can further include a functional group capable of being immobilized on a surface. Some examples of functional group capable of being immobilized on a surface include a carboxylic acid, thiol, β-diketone, silane, phosphate, phosphonate, alkyl, alkene, or alkyne, polymer, block co-polymer, and the like. In some other embodiments, the photoactive compound can be incorporated into polymers and/or hydrogels, for example to modify the molecule-surface interfacial tension or to modify steric constraints and make the photoactive portion of the molecule more accessible to molecules that are intended to be attached to the photoactive compound.

In one embodiment, the invention does not require the chemical modification of each molecule prior to deposition and it is not dependent on the molecular weight of the deposited molecule. Moreover, the invention can utilize bonds, including $sp^3$ bonds such as C—H bonds, S—H bonds, Si—H bonds, and the like, $sp^2$ bonds such as are present in alkenes, and sp bonds, such as are present in alkynes, which are present in many molecules (e.g., C—H bonds are readily found in carbohydrates). Reactive $sp^3$ bonds, such as anomeric C—H bonds that are present in carbohydrates, are useful in the invention. In a specific embodiment, the invention requires no chemical reagents beyond the monolayer or multilayer and generates very few byproducts.

The invention has a wide number of applications. For example, the invention can be utilized in tissue engineering, sensor fabrication, glycome sequencing, and in microarray construction for high-throughput characterization, such as the characterization of carbohydrate-related enzyme activity and carbohydrate interactions with cells, antibodies, proteins and microorganisms. Moreover, the surfaces may be used as biological sensors for identifying biological agents including antibodies and biological weapons.

In specific embodiments, the present invention provides a platform and method for screening antibody activity, such as binding activity towards various pathogens; photochemically linking at least one carbohydrate; and glycomic or proteomic studies, such as those aimed at the identification of biological agents, the discovery of new drugs, and understanding cellular processes.

Array Fabrication and Screening

In one embodiment, the invention provides methods for immobilizing an array of molecules on a surface. For example, a substrate can be coated with a photoactive monolayer. Molecules can be placed on the monolayer, for example at discrete locations. The molecules can be linked to the monolayer through a photochemical reaction, such as with irradiation, which causes covalent bonds to form between the molecules and the photoactive monolayer. The system, array, molecules, and/or monolayer may be irradiated through exposure to light, such as UV light. Unbound molecules can then be removed, such as by washing with appropriate aqueous or organic solvents. The photoactive monolayer can include compounds of Formulas (I), (II), or (III), or combinations thereof.

In another embodiment, the invention provides methods for immobilizing a patterned array of molecules on a surface. A mask containing the desired pattern or image can be placed over the photo-active molecule coated surface and irradiated though the mask. Alternatively, a robotic spotter can be utilized to place a photoactive compound and a molecule in a pattern on a photoactive surface, and the resultant patterned array can be irradiated. Other suitable methods to form a patterned array of immobilized carbohydrates will be readily apparent to one of ordinary skill in the art.

In one embodiment, the attachment of molecules onto a surface includes coating the molecules onto the surface.

The molecules to be attached to the surface can be attached at known, discrete locations on a surface. The compounds of formulas (I), (H), or (III) can be attached to an entire surface or one or more parts of the surface. Also, molecules can be attached to the compounds of Formula (I) or (II) at one or more parts of the surface, such as known, discrete and non-overlapping locations. The same molecule may be located at more than one part of the surface, and different molecules may be located at more than one part of the surface. The molecules can be attached to a photoactive compound of Formula (I) or (II) at one or more discrete parts of a surface at known locations.

The molecules used in the invention can be carbohydrates. The carbohydrates can be associated with, or present in or on on, pathogens, including bacteria, viruses, or parasites. Alternatively, the carbohydrates can bind to agents that recognize or bind to pathogens or toxins.

Illustrative pathogens or toxins can include *Bacillus anthracis, Vibrio cholerae, E. coli*, yeast, the causative organisms of tetanus and botulism, HIV such as HIV-1, orthomyoxyiridae, influenza viruses, SARS-CoV, *Bacillus cereus, Brucella abortus, Brucella melitensis, Brucella suds, Campylobacter jejuni, Clostridium botulirum, Clostridium perfringens, Enterohemorrhagic E. Coli, Enterotoxigenic E. coli, Listeria monocytogenes, Salmonella, Shigella, Staphylococcus aureus, Vibrio parahaemolyticus, Vibrio vulnificus, Yersinia enterocolytica* and *Yersinia pseudotuberculosis*, hepatitis A, norwalk-like viruses, rotavirus, astroviruses, calciviruses, adenoviruses, and parvoviruses, *Cryptosporidium parvum, Cyclospora cayetanensis, Entamoeba histolytica, Giardia lamblia, Toxoplasma gondii, Trichinella spiralis, Clostridium botulinum, Yersinia pestis, Francisella tullarensis, Brucella* species epsilon toxin from *Clostridium perfringens, Salmonella* species, *Escherichia coli* 0157:H7, *Shigella, Cryptosporidium parrum, Burkholderia mallet, Burkholderia pseudomallei, Chlamydia psittaci, Coxiella burnetii*, Ricin toxin from *Ricinus communis, Staphylococcal enterotoxin B., Rickettsia prowazekii*, ciguatera toxin, shellfish toxins, floviruses, ebola virus, Marburg virus, arenaviruses, Lassa virus, Machupo virus, hantavirus, variola major, hemorrhagic fever virus, Nipah virus, alphaviruses, Venezuelan equine encephalitis, eastern equine encephalitis, and western equine encephalitis, and toxins therefrom.

A biomarker in the present invention can be an antibody or a carbohydrate. A biomarker can include an immunoglobulin, a monoclonal antibody, polyclonal antibody, Fv fragment, single chain Fv (scFv) fragment, Fab' fragment, $F(ab')_2$ fragment, single domain antibody, camelized antibody, humanized antibody, diabodies, tribodies, and tetrabodies. In one embodiment, a biomarker can be an agent.

In a more specific embodiment, the carbohydrates used in the invention may correspond to carbohydrates from natural sources or synthetic carbohydrates. The carbohydrates can correspond to those present on or isolated from pathogens, such as *Bacillus anthracis*. The carbohydrates listed below and described in Table 1, and glycosides and combinations thereof, can be employed. In one embodiment, carbohydrates may include both anomers. In a more specific embodiment, carbohydrates may include both anomers of each monosaccharide present in an oligo- or polysaccharide, in any ratio, or anomers of a subset of all of the monosaccharides present in an oligo- or polysaccharide. Carbohydrates used in the invention may be derivatized or underivatized, and may be obtained from commercial and non-commercial sources, such as the NIH, or may be synthesized according to synthetic procedures available in the literature.

In another aspect, the invention also provides carbohydrate arrays formed by the methods of the invention. The array of the invention can use any number of carbohydrates, including a plurality of carbohydrates. In more specific embodiments, the array includes from 5 to 1,000,000; 5 to 1,000; 10 to 100; or 35 carbohydrates. In another embodiment, the array includes carbohydrates specific to pathogens or which are recognized by antibodies to pathogens.

In one embodiment, the invention includes an array that includes one or more of the following carbohydrates:

2-O-methyl-4-(3-hydroxy-3-methylbutamido)-4,6-dideoxy-D-glucose;
2-O-methyl-4-(3-hydroxy-3-methylbutamido)-4,6-dideoxy-β-D-glucose;
2-O-methyl-4-(3-hydroxy-3-methylbutamido)-4,6-dideoxy-α-D-glucose;
2-O-methyl-4-(3-hydroxy-3-methylbutamido)-4,6-dideoxy-β-D-glucopyranosyl-(1→3)-α-L-rhamnopyranose;
2-O-methyl-4-(3-hydroxy-3-methylbutamido)-4,6-dideoxy-β-D-glucopyranosyl-(1→3)-β-L-rhamnopyranose;
2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranose;
α-L-rhamnopyranosyl-(1→3)-α-L-rhamnopyranose;
2-O-methyl-4-(3-hydroxy-3-methylbutamido)-4,6-dideoxy-β-D-glucopyranosyl-(1→3)-α-L-rhamnopyranosyl-(1→3)-β-L-rhamnopyranose;
2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-L-rhamnopyranose;
2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-α-L-rhamnopyranose;
2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-β-L-rhamnopyranose,
α-L-rhamnopyranosyl-(1→3)-α-L-rhamnopyranosyl-(1→2)-L-rhamnopyranose;
α-L-rhamnopyranosyl-(1→3)-α-L-rhamnopyranosyl-(1→2)-β-L-rhamnopyranose;
α-L-rhamnopyranosyl-(1→3)-α-L-rhamnopyranosyl-(1→2)-α-L-rhamnopyranose;
5-(Methoxycarbonyl)-pentyl-4-(3-hydroxy-3-methylbutanamido)-2-O-methyl-4,6-dideoxy-α-D-glucopyranoside;
5-(Methoxycarbonyl)-pentyl-4-(3-hydroxy-3-methylbutanamido)-2-O-methyl-4,6-dideoxy-α-D-glucopyranoside;
5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranoside;
5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranoside;
5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranoside;
5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranoside;
5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranosyl-(1→2)-α-L-rhamnopyranoside;
5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranosyl-(1→2)-β-L-rhamnopyranoside;
n-Pentenyl 4,6-Dideoxy-4-(3-hydroxy-3-methylbutanamido)-2-O-methyl-β-D-glucopyranose;
n-Pentenyl 4,6-Dideoxy-4-(3-hydroxy-3-methylbutanamido)-2-O-methyl-β-Dglucopyranosyl-(1→3)-α-L-rhamnopyranose;
n-Pentenyl 4,6-Dideoxy-4-(3-hydroxy-3-methylbutanamido)-2-O-methyl-β-D-glucopyranosyl-(1→3)-β-L-rhamnopyranose;
n-Pentenyl 4,6-Dideoxy-4-(3-hydroxy-3-methylbutanamido)-2-O-methyl-β-D-glucopyranosyl-(1→3)-α-L-rhamnopyranosyl-(1→3)-α-L-rhamnopyranose;
n-Pentenyl 4,6-Dideoxy-4-(3-hydroxy-3-methylbutanamido)-2-O-methyl-β-D-glucopyranosyl-(1→3)-β-L-rhamnopyranosyl-(1→3)-α-L-rhamnopyranose;
L-rhamnopyranosyl-(1→3)-α-L-rhamnopyranosyl-(1→2)-α-L-rhamnopyranose;
n-Pentenyl 4,6-Dideoxy-4-(3-hydroxy-3-methylbutanamido)-2-O-methyl-β-Dglucopyranosyl-(1→3)-α-L-rhamnopyranosyl-(1→3)-α-L-rhamnopyranosyl-(1→2)-α-L-rhamnopyranose; or
n-Pentenyl 4,6-Dideoxy-4-(3-hydroxy-3-methylbutanamido)-2-O-methyl-β-Dglucopyranosyl-(1→3)-β-L-rhamnopyranosyl-(1→3)-α-L-rhamnopyranosyl-(1→2)-α-L-rhamnopyranose,
5-(Methoxycarbonyl)-pentyl-4-(3-hydroxy-3-methylbutanamido)-2-O-methyl-4,6-dideoxy-β-D-glucopyranosyl-(1→3)-α-L-rhamnopyranosyl-(1→3)-α-L-rhamnopyranosyl-(1→2)-β-L-rhamnopyranose;
Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside,
Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-tetrakis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

[Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside]$_5$-BSA;

[Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA;

[Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA; or glycosides thereof; or combinations thereof.

In another embodiment, the carbohydrates listed in Table 1 can be used in the invention.

TABLE 1

| ID# | Abbreviation | Structural Information |
|---|---|---|
| 1 | Ant | 5-(Methoxycarbonyl)-pentyl 4-(3-hydroxy-3-methylbutanamido)-2-O-methyl-4,6-dideoxy-β-D-glucopyranoside |
| 2 | Ant-α-Rha | 5-(Methoxycarbonyl)-pentyl 4-(3-hydroxy-3-methylbutanamido)-2-O-methyl-4,6-dideoxy-β-D-glucopyranosyl-(1→3)-α-L-rhamnopyranoside |
| 3 | Ant-(1→3)-α-Rha-(1→2)-α-Rha | 5-(Methoxycarbonyl)-pentyl 4-(3-hydroxy-3-methylbutanamido)-2-O-methyl-4,6-dideoxy-β-D-glucopyranosyl-(1→3)-α-L-rhamnopyranosyl-(1→2)-α-L-rhamnopyranoside |
| 4 | Ant-(1→3)-α-Rha-(1→3)-α-Rha-(1→2)-β-Rha | 5-(Methoxycarbonyl)-pentyl 4-(3-hydroxy-3-methylbutanamido)-2-O-methyl-4,6-dideoxy-β-D-glucopyranosyl-(1→3)-α-L-rhamnopyranoyl-(1→3)-α-L-rhamnopyranosyl-(1→2)-β-L-rhamnopyranoside |
| 5 | Ant-(1→3)-α-Rha-(1→3)-α-Rha-(1→2)-α-Rha | 5-(Methoxycarbonyl)-pentyl 4-(3-hydroxy-3-methylbutanamido)-2-O-methyl-4,6-dideoxy-β-D-glucopyranosyl-(1→3)-α-L-rhamnopyranoyl-(1→3)-α-L-rhamnopyranosyl-(1→2)-α-L-rhamnopyranoside |
| 6 | Rha | L-Rhamnose |
| 7 | Fuc | D-Fucose |
| 8 | Gal | D-Galactose |
| 9 | Glc | D-Glucose |
| 10 | Man | D-Mannose |
| 11 | GalNAc | N-acetyl-2-amino-2-deoxy-D-galactose |
| 12 | Ara | L-Arabinose |
| 13 | Man | L-Mannose |
| 14 | α-Rha | 5-(Methoxycarbonyl)-pentyl-α-L-rhamnopyranoside |
| 15 | β-Rha | 5-(Methoxycarbonyl)-pentyl-β-L-rhamnopyranoside |
| 16 | α-Rha-(1→3)-α-Rha | 5-(Methoxycarbonyl)-pentyl-α-L-rhamnopyranosyl-(1→3)-α-L-rhamnopyranoside |
| 17 | α-Rha-(1→3)-α-Rha-(1→2)-α-Rha | 5-(Methoxycarbonyl)-pentyl-α-L-rhamnopyranosyl-(1→3)-α-L-rhamnopyranosyl-(1→2)-α-L-rhamnopyranoside |
| 18 | Rha-(1→2)-α-Rha | 5-(Methoxycarbonyl)-pentyl-α-L-rhamnopyranosyl-(1→2)-α-L-rhamnopyranoside |
| 19 | Rha-(1→2)-β-Rha | 5-(Methoxycarbonyl)-pentyl-α-L-rhamnopyranosyl-(1→2)-β-L-rhamnopyranoside |
| 20 | α-Rha-(1→3)-α-Rha-(1→2)-β-Rha | 5-(Methoxycarbonyl)-pentyl-α-L-rhamnopyranosyl-(1→3)-α-L-rhamnopyranosyl-(1→2)-β-L-rhamnopyranoside |
| 21 | α-Rha-(1→2)-Gal | Methyl α-L-rhamnopyranosyl-(1→2)-D-galactopyranoside |
| 22 | Me α-GlcNAc-(1→3)-α-Rha-(1→3)-α-Rha-(1→2)-α-Gal | Methyl 2-acetamido-2-deoxy-α-D-glucopyranosyl-(1→3)-α-L-rhamnopyranosyl-(1→3)-α-L-rhamnopyranosyl-(1→2)-α-D-galactopyranoside |
| 23 | Me α-Rha-(1→2)-α-Gal-(1→3)-α-GlcNAc | Methyl α-L-rhamnopyranosyl-(1→2)-α-D-galactopyranosyl-(1→3)-2-acetamido-2-deoxy-α-D-glucopyranoside |
| 24 | Me α-Rha-(1→3)-α-Rha | Methyl α-L-rhamnopyranosyl-(1→3)-α-L-rhamnopyranoside |
| 25 | Me α-Rha-(1→3)-α-Rha-(1→2)-α-Gal | Methyl α-L-rhamnopyranosyl-(1→3)-α-L-rhanmopyranosyl-(1→2)-α-D-galactopyranoside |
| 26 | Me α-Rha-(1→3)-α-Rha-(1→2)-α-Gal-(1→3)-α-GlcNAc | Methyl α-L-rhamnopyranosyl-(1→3)-α-L-rhanmopyranosyl-(1→2)-α-D-galactopyranosyl-(1→3)-2-acetamido-2-deoxy-α-D-glucopyranoside |
| 27 | Ogawa-Tri | Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside |

TABLE 1-continued

| ID# | Abbreviation | Structural Information |
|---|---|---|
| 28 | Ogawa-Tetra | Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside |
| 29 | Ogawa-Penta | Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside |
| 30 | Ogawa-Hexa | Methyl 2-O-methyl-4,6-dideoxy-4-(3-deoxy-L-glycero-tetronamido)-D-mannopyranosyl-(1→2)-tetrakis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside |
| 31 | Ogawa-Tri-BSA | [Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside]$_5$-BSA |
| 32 | Ogawa-Tetra-BSA | [Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA |
| 33 | Ogawa-Penta-BSA | [Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA |
| 34 | Isolichenin | α-(1→3)-Glucan |
| 35 | Pn23 | *Streptococcus pneumoniae* type 23 capsular polysaccharide (D-Gal:D-Glu:L-Rha:Glycerol:Phosphorus = 1:1:2:0.6:1 and with the terminal L-Rha as a key residue of a dominant antigenic determinant) |

The carbohydrates of the invention can include the α- and β-anomers of each monosaccharide, or a combination of both, unless otherwise specified. Other molecules than can be immobilized on a surface and used in the invention will be readily apparent to one of skill in the art. In some embodiments, each molecule to be deposited on the surface may be deposited in more than one spot.

In some embodiments, the deposition of a molecule on a surface or a monolayer, is repeated at least twice in at least two different locations, creating at least two identical spots on the array. An array can thus be generated with three, four, five, or more identical spots of a molecule, such as a carbohydrate. A molecule can be spotted on the array at differing concentrations as measured by weight percentages or concentrations or by molar percentages or concentrations. In one embodiment of the invention, the molecules deposited on the surface or monolayer are carbohydrates.

One aspect of the present invention is a method for determining the presence of an antibody that specifically binds *Bacillus anthracis* in a sample, which includes contacting the sample with a carbohydrate array of the invention; and determining whether a carbohydrate at a known location on the surface has an antibody that specifically binds *Bacillus anthracis* bound thereto. The sample is from a subject, such as a human. The determination may be accomplished using secondary antibodies to the *B. anthracis*-binding antibody, where the secondary antibody is labeled with a detectable probe, such as a fluorescent or radioactive molecule or an enzyme conjugate that is used in a colorimetric assay.

Figure 1:
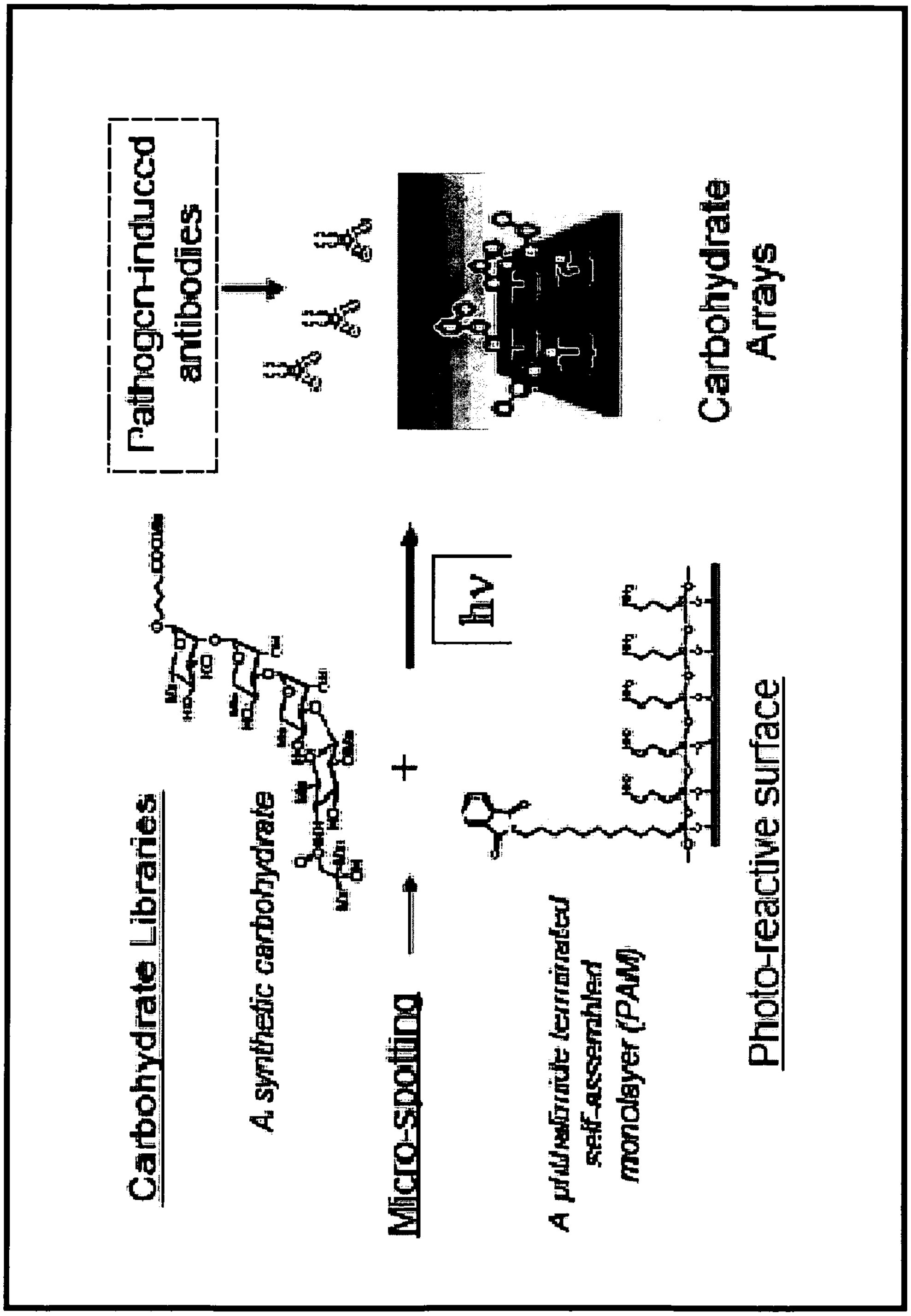
FIG. 1 schematically depicts a method of the invention.

FIG. 1 depicts an application of a photo-generated carbohydrate array to elucidate the presence of pathogen-induced antibodies. This method involves covalently bonding a carbohydrate to a phthalimide terminated self-assembled mixed monolayer using irradiation (hν). Irradiation induces a photochemical reaction that covalently links the carbohydrates to the monolayer, such as is depicted in FIG. 4. A sample that includes antibodies that were induced by exposure to a pathogen, is subjected to the resultant carbohydrate array. The antibodies bind to the carbohydrate epitopes for which they have affinity, then are visualized, such as by labeled secondary antibodies or an enzyme-linked immunosorbent assay (ELISA). The label can be a chromogenic or fluorescent molecule, such as fluorescein, FITC, or green fluorescent protein, or the like.

Some embodiments of the invention relate to methods for immobilizing molecules on a surface. Methods of the invention can include immobilizing on a surface of a substrate a one or more photoactive compounds that are capable of forming at least one covalent bond with a nearby molecule after irradiation; applying at least one molecule, such as a carbohydrate, onto the photoactive compounds on the surface; and irradiating the photoactive compounds, enabling a photochemical reaction between the photoactive compounds and the carbohydrate, resulting in at least one covalent bond between the photoactive compound and the carbohydrate and immobilizing the carbohydrate at the surface.

In one embodiment, a plurality of different carbohydrates are covalently attached to a one or more compounds of Formula I that have been immobilized on a surface and that form a photoactive surface on top of the surface to which the compounds are immobilized. Each type of different carbohydrate can be spatially segregated on the photoactive surface.

Other embodiments of the invention also relate to methods for immobilizing molecules on a surface. Methods of the invention can include (1) immobilizing on a surface a photoactive compound capable of forming covalent bonds with nearby molecules after irradiation; (2) applying a molecule to the photoactive compound; and (3) irradiating the photoactive compound, wherein a photochemical reaction between the photoactive compound and the molecule results in covalent links between the molecule and the photoactive compound to immobilize the molecule near the surface. In certain embodiments, the photoactive compound can be immobilized on the surface as a self-assembled monolayer (see FIG. 1). In other embodiments, the photoactive compound can be immobilized on the surface as a multilayer.

In other embodiments, methods of the invention can include (1) immobilizing on a surface a composition that includes a photoactive compound capable of forming covalent bonds with nearby molecules after irradiation and a second compound that can increase the affinity of desired molecules to the composition; (2) applying a molecule to the composition; and (3) irradiating the composition, wherein a photochemical reaction between the photoactive compound and the molecule results in covalent links between the molecule and the photoactive compound to immobilize the molecule near the surface. In certain embodiments, the composition can be immobilized on the surface as a self-assembled monolayer. In other embodiments, the photoactive compound can be immobilized on the surface as a multilayer.

In some embodiments, the molecule that forms covalent links with the photoactive compound can be a carbohydrate.

In certain embodiments, the photoactive compound can be immobilized on the surface of the substrate as a self-assembled monolayer (SAM). In one embodiment, a photochemical reaction described herein includes a radical. In another embodiment, the photochemical reaction does not include a carbene. In yet another embodiment, the substrate does not include a protein.

One embodiment of the invention is the photo-generation of epitope-specific carbohydrate arrays. In one embodiment, a photoactive surface is utilized for the covalent immobilization and patterning of carbohydrates onto a substrate such as glass. This method can employ a glass slide coated with a self-assembled monolayer that presents photoactive chromophores, such as phthalimides, at the air-monolayer interface. Upon exposure to UV radiation, for example at a wavelength of 280 nm to 400 nm or 300 nm, the phthalimide end-groups graft the carbohydrates by hydrogen abstraction and radical recombination.

A radical-quenching substituent on the photoactive moiety is believed to result in inferior reactivity of the photoactive moiety and consequently poorer immobilization of any molecule to the photoactive surface. For example, it is believed that direct amino substitution on the photoactive phthalimide moiety results in poor immobilization of a molecule to the photoactive surface.

One advantage of the invention is that the efficacy of carbohydrate immobilization to the instant array is independent of the molecular weights of spotted carbohydrates. Another advantage of photochemical immobilization is the ability to produce epitope-specific carbohydrate arrays using unmodified carbohydrates. This technology was applied to display a panel of carbohydrate structures, including synthetic fragments and derivatives of the anthrose-containing tetrasaccharide of the *B. anthracis* exosporium and a number of control carbohydrate antigens (see Table 1), for immunological characterization.

The invention also provides methods for immobilizing a patterned array of molecules on a surface. In one embodiment, a mask containing the desired pattern or image can be placed over the coated surface and the surface can be irradiated though the mask. Alternatively, a robotic spotter can be utilized. The robotic spotter can be used to create patterned areas containing a photoactive compound and a molecule, either concurrently or step-wise, and the patterned array can be irradiated. Other suitable methods to form a patterned array of immobilized carbohydrates will be readily apparent to one of ordinary skill in the art.

The photoactive compound and/or the immobilized molecule can be formed as a coating on a surface, and at various thicknesses. For example, the photoactive compound and/or the immobilized molecule may form a coating with a thickness of less than 1 nm, 2 nm, 5 nm, 10 nm, 20 nm, 50 nm, 100 nm and the like. For example, if a monolayer of photoactive compound and/or the immobilized molecule is formed on the surface, the thickness can depend on the molecular weight of the photoactive compound and/or the immobilized molecule. In some embodiments, the photoactive compound and/or the immobilized molecule may be applied to the surface by spin coating, spray coating, robotic spotting, or any other conventional techniques known in the art to obtain a desired coating of a compound or molecule.

In other embodiments, the molecules are linked to a compound of Formula (I) or (II) on a surface through a radical reaction. The radical reaction can be initiated using light, such as ultraviolet light, or by single-electron transfer. The radical reaction may be initiated by electron transfer to a molecule of Formula (I) or (II) an electron from a molecule such as AIBN, tributyl tin hydride, or an amine or sulfide, such as a thioether, or the like.

In some embodiments, the photoactive compound can further include a functional group capable of being immobilized on a surface. In some cases, this immobilization is through a covalent bond. Some examples of functional group capable of being immobilized on a surface include a carboxylic acid, thiol, β-diketone, silane, phosphate, phosphonate, alkyl, alkene, alkyne, polymer, block co-polymer, and the like. In other embodiments, the photoactive compound can be incorporated into polymers and/or hydrogels to modify the molecule-surface interfacial tension or to modify steric constraints that may make the photoactive portion of the molecule inaccessible. In specific embodiments, the compound may be immobilized via a chemical reaction as follows, a thiol-containing compound can be covalently attached to a gold surface, a silane, phosphate, or phosphonate (such as an silane ether or phosphate or phosphonate ester) can be covalently attached to a surface comprising terminal hydroxyl groups via ether or ester exchange. In a specific embodiment, the photoactive compound contains a silane such as a silane ether, and the covalent immobilization is accomplished through exchange of an ether group thereon for a surface hydroxyl group, using methods as described herein and methods as will be apparent to one of skill in the art.

Any suitable molecule may be covalently bonded to the surface. In one embodiment, carbohydrates, glycolipids, glycopolymers, proteoglycans, and glycoproteins are useful in the invention. For example, carbohydrates, such as monosaccharides, disaccharides, trisaccharides, tetrasaccharides, oligosaccharides, polysaccharides, glycosides thereof, and the like, can be utilized in the invention. In some embodiments, the carbohydrate can be a simple carbohydrate, such as glucose or sucrose. In other embodiments, one or more dextrans ranging from 20-2000 kDA can be utilized. In some embodiments, the carbohydrates can be underivatized carbohydrates, without chemical modification. Similar molecules that can be immobilized on a surface will be readily apparent to one of ordinary skill in the art.

In some embodiments the molecule that can be covalently bonded to the surface elicits an immune response in an organism, such as an animal, including a mammal, and further including a human. Such a molecule can be a carbohydrate. In some cases, the response elicited will be the production of antibodies against the molecule.

In one embodiment, the invention does not require the chemical modification of a molecule prior to deposition. The derivatization also may not be dependent on the molecular weight of the molecule. In some embodiments, the photochemical reaction of the invention can utilize bonds, including $sp^3$ bonds such as C—H bonds, S—H bonds, and Si—H bonds, $sp^2$ bonds such as are present in alkenes, and sp bonds, such as are present in alkynes, and the like, which are present in many molecules (e.g., C—H bonds are readily found in carbohydrates). In other embodiments, the invention requires no chemical reagents beyond the photoactive monolayer and generates very few byproducts.

In one embodiment, the invention uses biomarkers unique to *B. anthracis*.

Another embodiment of the invention is the development of new, safer anthrax vaccines to block the anthrax infection. An efficient means to determine the immune response elicited by a candidate vaccine would greatly facilitate such a development. If *B. anthracis* spores express potent immunogenic carbohydrate moieties, immunization with the spores should elicit antibodies specific for these carbohydrate structures. Such antibody reactivities could then be detected by carbohydrate arrays that display the carbohydrate structures recognized by the antibodies. One embodiment of the invention is to identify highly specific immunogenic targets, such as those displayed on *B. anthracis* spores. Highly specific immunogenic targets such as surface-exposed carbohydrate moieties characteristic for a given microbe may serve as key biomarkers for pathogen identification, diagnosis, and vaccine development.

The invention has a wide number of applications. For example, the invention can be utilized in pathogen detection, the determination of exposure to a pathogen, the screening of vaccine candidates, the determination of the immune response elicited by a vaccine or vaccine candidate, the elucidation of the binding epitope of carbohydrate-binding proteins including antibodies, sensor fabrication, glycome sequencing, high-throughput array construction, and high-throughput characterization of carbohydrate enzyme activity and carbohydrate interactions with cells, antibodies, proteins and microorganisms.

In another embodiment, the surfaces may serve as sensors for identifying biological entities, such as cancer cells, pathogens, or biological weapons. The invention also provides for screening antibody activity towards various organisms, including pathogens; photopatterning a carbohydrate, biological or synthetic; glycomic and proteomic studies aimed at the discovery of new drugs and vaccines, and the understanding of cellular processes.

Arrays of the invention may also be used to screen for agents that recognize carbohydrates. The agents may be proteins, and the agents may be associated with pathogens, including agents that are present on a pathogen or agents that bind to a pathogen. The carbohydrates may be specific to pathogens, and the agents may be biomarkers, proteins, such as antibodies, and/or synthetic molecules. The arrays may be used to screen for or otherwise develop compositions which interfere with, or inhibit, pathogen binding. In one embodiment, the carbohydrate can be a biomarker for a pathogen or a disease.

The invention also includes methods for diagnosing a disease or determining the exposure to one or more pathogens in a subject and/or a sample, such as a sample of biological origin, including from a subject. The subject can be an animal, such as a mammal, including a human. The invention also includes methods for detecting or determining the presence of antibodies to a disease or pathogen in a subject or a sample, such as a biological sample, including a sample from a subject. In one embodiment, a carbohydrate or an antibody can be a biomarker for a disease.

EXAMPLES

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of the invention. All changes, modifications, and variations coming within the meaning and range of equivalency of the claims are to be considered within their scope.

Further description of some examples disclosed herein can be found in U.S. Provisional Patent Application Nos. 60/776,096, 60/735,402, and 60/843,674, each of which are hereby incorporated by reference in their entireties.

Example 1

Synthesis of Compound I-1

A 3.3 mmol portion of 11-bromoundecanetrimethoxysilane (Gelest) was added to a solution of an equimolar amount of potassium phthalimide (Aldrich) in 60 mL of anhydrous DMF (Aldrich). The solution was stirred overnight at room temperature (RT) under argon. Chloroform (50 mL) was added. The solution was transferred to a separatory flask containing 50 mL of $H_2O$. The aqueous layer was separated and then extracted with two 20 mL portions of chloroform. The combined chloroform extract was washed with several 20 mL portions of $H_2O$. The chloroform was removed by rotoevaporation, and residual DMF was removed on a high vacuum line to give a pale yellow liquid (0.99 g, 72% yield). The compound was used without further purification. For self-assembly experiments, residual DMF was not removed. $^1H$ NMR: ($CDCl_3$) δ 7.82 (m, 2H), 7.69 (m, 2H), 3.66 (t, J=7 Hz, 2H), 3.55 (s, 9H), 1.44-1.15 (m, 18H), 0.71-0.51 (m, 2H). LRMS-$FAB^+$ (m/z): (M-H) 420.2 (experimental), 420.2 (calculated); (M-$OCH_3$) 390.1 (experimental), 390.2 (calculated).

Fabrication of Mixed Monolayers:

A robotic spotter was used to deliver polysaccharides to the surface. However, the thermodynamic parameters of the surface needed to be adjusted in order to transfer a detectable amount of carbohydrates from the pin of the spotter to SAM 1 (below). In order to make the surface more attractive to carbohydrates, mixed monolayers were made from a solution containing a 5:1 ratio of aminopropyltrimethoxy silane to compound I-1. Presumably, the hydrophilic amine group interacts more favorably with the carbohydrates as compared to the more hydrophobic phenyl ring of compound I-1, decreasing the interfacial tension between the carbohydrate and the surface, allowing for a sufficient amount of carbohydrates to be adsorbed to the surface for subsequent photoimmobilization. Alternatively, a 20:1 mixture was used.

Preparation of SAM 1:

Substrates consisted of glass (ArrayIt), quartz (SPI) or silicon (wafer world). Substrates and glassware were cleaned by boiling in a "piranha" solution (7:3 sulfuric acid:$H_2O_2$) for one hour followed by an extensive rinse with water and methanol. Substrates were dried with a stream of argon and a 1 mmol solution of compound I-1 in anhydrous toluene (Aldrich) and a solution containing a 5× molar amount of aminopropyltrimethoxy silane (Gelest) relative to compound I-1 were simultaneously added to the substrate. The solution was kept under argon and left undisturbed for twelve hours. The surface was then removed and baked for two hours at 110° C. The resulting self-assembled monolayers were rinsed with toluene and sonicated three times for two minutes each in toluene, toluene:methanol 1:1, and methanol, yielding SAM 1. Coated substrates were kept in argon-purged vials until further use.

Alternatively, SAM 2, containing a 20:1 ratio of aminopropyltrimethoxy silane to phthalimide was constructed. Mixed monolayers were formed by the method for SAM 1, above, substituting a solution containing a 20:1 ratio of aminopropyltrimethoxy silane to compound I-1 in anhydrous toluene for the 5:1 solution used above. The solution was mixed in a vial containing anhydrous toluene. The solution was then transferred to a vial, capped with a rubber septum, containing the microscope slide under argon. The procedure then continued as above.

Microarray Construction

The carbohydrates of Table 1 were individually dissolved in saline (0.9% NaCl) at a given concentration and were spotted in triplicate in parallel. The initial amount of carbohydrate spotted was 0.35 ng per spot and was further diluted by serial dilutions of 1:5 thereafter. A high-precision robot designed to produce cDNA microarrays (PIXSYS 5500C, Cartesian Technologies Irvine, Calif.) was utilized to spot carbohydrate antigens onto chemically modified glass slides as described.

Photo-Coupling of Carbohydrates

After microarray spotting, the SAM 1 slides were air-dried and placed in a quartz tube. The sealed tube was subsequently purged with argon or nitrogen before irradiation. UV irradiation was conducted by placing the quartz tube under a desktop lamp containing a 300 nm Rayonet bulb for one hour. Precaution was made to avoid skin and eye contact with the radiation during the irradiation process.

Microarray Screening

Immediately before use, the printed microarrays were rinsed and washed with PBS (PH 7.4) two times with five minutes of incubation in each washing step. They were then "blocked" by incubating the slides in 1% BSA in PBS containing 0.05% NaN3 at room temperature (RT) for 30 minutes. Antibody staining was conducted at RT for one hour at given dilutions in 1% BSA PBS containing 0.05% NaN3 and 0.05% Tween 20. The stained slides were rinsed five times with PBS containing 0.05% Tween 20 after each staining step. A ScanArray 5000A Standard Biochip Scanning System (PerkinElmer, Torrance, Calif.) equipped with multiple lasers, emission filters and ScanArray Acquisition Software was used to scan the microarray. Fluorescence intensity values for each array spot and its background were calculated using ScanArray Express (PerkinElmer, Torrance, Calif.). The screening data are depicted in FIG. 2A and Table 2, below.

Figure 2A:
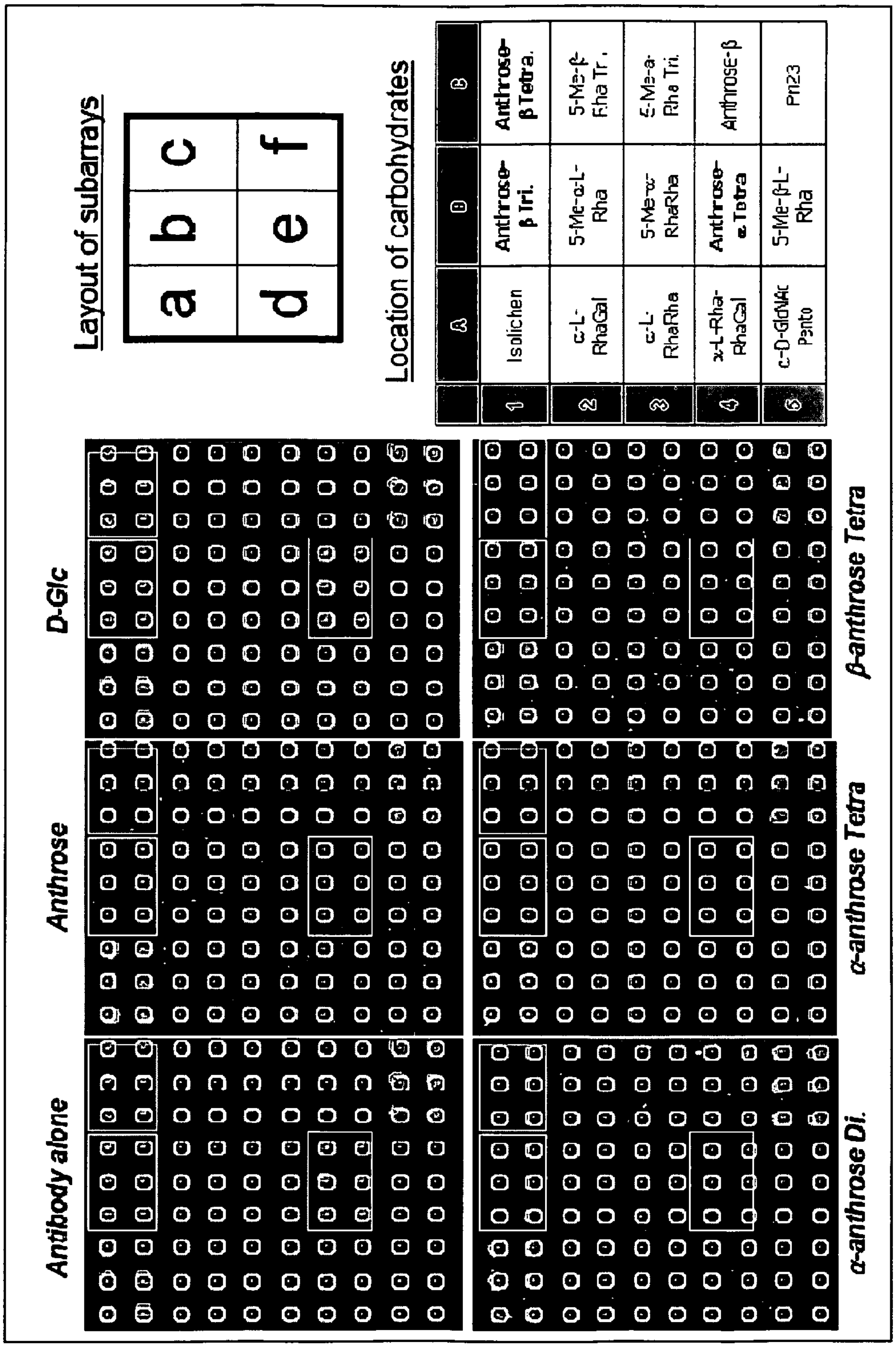
FIG. 2A illustrates an application of a photo-generated carbohydrate array of the invention.

FIGS. 2A and B depict portions of an array of the invention, which was created when a panel of thirty-five mono-, oligo- and polysaccharides, listed in Table 1, were spotted onto the surface of photoactive glass slides followed by UV-irradiation to induce covalent coupling of the carbohydrates to the photoactive surface, as described above. The photo-generated carbohydrate arrays were stained with rabbit anti-*B. anthracis* spore polyclonal IgG antibodies at 10 or 20 μg/ml in the absence or presence of carbohydrate inhibitors (0.25 mg/ml) as specified in Table 2 for each subarray. The bound rabbit IgG was revealed by a fluorescent-labeled anti-rabbit IgG antibody. The images of the subarrays a-f display a portion of the stained carbohydrate arrays: (a) no inhibitor; (b) anthrose; (c) D-glucose; (d) α-anthrose trisaccharide; (e) α-anthrose tetrasaccharide; (f) β-anthrose tetrasaccharide. The locations of surface-bound anthrose-containing carbohydrates that are recognized by the antibody in the absence of inhibitor are highlighted by boxes in each subarray a-f and as shown in FIG. 2B: the top left box in each subarray indicates the presence of β-anthrose-trisaccharide; the top right box in each subarray indicates the presence of β-anthrose-tetrasaccharide; and the bottom box in each subarray indicates the presence of α-anthrose-tetrasaccharide. The data sets resulting from the screen depicted in FIG. 2A are shown in Table 2.

TABLE 2

| Saccharides spotted | | *IgG reactivities (ratio of signal/background) | | |
|---|---|---|---|---|
| Id[#] | Short name** | Array location | Mean | SD |
| Subarray-a, IgG 20 μg/ml: No inhibitor | | | | |
| 34 | Isolichenin | A1 | 36.32 | 1.52 |
| 21 | Me α-L-RhaGal | A2 | 1.08 | 0.05 |
| 24 | Me L-α-Rha((1→3)Rha | A3 | 1.02 | 0.04 |
| 25 | Me α-L-RhaRhaGal | A4 | 1.02 | 0.04 |
| 22 | Me α-D-GlcNAcRhaRhaGal | A5 | 0.95 | 0.03 |
| 3 | 5-Methoxycarbonyl Anthrose-α-Tri | B1 | 2.73 | 0.09 |
| 14 | 5-Methoxycarbonyl α-L-Rha | B2 | 0.97 | 0.03 |
| 16 | 5-Methoxycarbonyl αRha(1→3)Rha | B3 | 1.00 | 0.04 |
| 5 | 5-Methoxycarbonyl Anthrose-α-Tetra | B4 | 5.19 | 0.31 |
| 15 | 5-Methoxycarbonyl β-L-Rha | B5 | 0.95 | 0.01 |
| 4 | 5-Methoxycarbonyl Anthrose-β-Tetra | C1 | 5.16 | 0.58 |
| 20 | 5-Methoxycarbonyl β-RhaRhaRha | C2 | 0.95 | 0.04 |
| 17 | 5-Methoxycarbonyl α-RhaRhaRha | C3 | 0.98 | 0.01 |
| 1 | 5-Methoxycarbonyl Anthrose | C4 | 1.44 | 0.08 |
| 35 | Pn23 polysaccharide | C5 | 12.35 | 5.24 |
| Subarray-b, IgG 10 μg/ml: | | 5-Methoxycarbonyl Anthrose 0.25 mg/ml | | |
| 34 | Isolichenin | A1 | 11.85 | 0.02 |
| 21 | Me α-L-RhaGal | A2 | 0.96 | 0.06 |
| 24 | Me L-α-Rha((1→3)Rha | A3 | 0.96 | 0.04 |
| 25 | Me α-L-RhaRhaGal | A4 | 0.97 | 0.04 |
| 22 | Me α-D-GlcNAcRhaRhaGal | A5 | 0.96 | 0.02 |
| 3 | 5-Methoxycarbonyl Anthrose-α-Tri | B1 | 1.08 | 0.05 |
| 14 | 5-Methoxycarbonyl α-L-Rha | B2 | 0.93 | 0.03 |
| 16 | 5-Methoxycarbonyl αRha(1→3)Rha | B3 | 0.95 | 0.04 |
| 5 | 5-Methoxycarbonyl Anthrose-α-Tetra | B4 | 0.96 | 0.07 |
| 15 | 5-Methoxycarbonyl β-L-Rha | B5 | 0.93 | 0.07 |

TABLE 2-continued

| Saccharides spotted | | *IgG reactivities (ratio of signal/background) | | |
|---|---|---|---|---|
| Id# | Short name** | Array location | Mean | SD |
| 4 | 5-Methoxycarbonyl Anthrose-β-Tetra | C1 | 0.96 | 0.02 |
| 20 | 5-Methoxycarbonyl β-RhaRhaRha | C2 | 1.04 | 0.05 |
| 17 | 5-Methoxycarbonyl α-RhaRhaRha | C3 | 0.97 | 0.05 |
| 1 | 5-Methoxycarbonyl Anthrose | C4 | 0.93 | 0.03 |
| 35 | Pn23 polysaccharide | C5 | 5.27 | 1.36 |
| | Subarray-c, IgG 20 μg/ml: | D-Glu 0.25 mg/ml | | |
| 34 | Isolichenin | A1 | 34.88 | 1.04 |
| 21 | Me α-L-RhaGal | A2 | 1.14 | 0.00 |
| 24 | Me L-α-Rha((1→3)Rha | A3 | 0.99 | 0.01 |
| 25 | Me α-L-RhaRhaGal | A4 | 1.04 | 0.06 |
| 22 | Me α-D-GlcNAcRhaRhaGal | A5 | 1.06 | 0.04 |
| 3 | 5-Methoxycarbonyl Anthrose-α-Tri | B1 | 4.09 | 0.24 |
| 14 | 5-Methoxycarbonyl α-L-Rha | B2 | 1.03 | 0.01 |
| 16 | 5-Methoxycarbonyl αRha(1→3)Rha | B3 | 1.05 | 0.05 |
| 5 | 5-Methoxycarbonyl Anthrose-α-Tetra | B4 | 6.60 | 0.13 |
| 15 | 5-Methoxycarbonyl β-L-Rha | B5 | 1.07 | 0.03 |
| 4 | 5-Methoxycarbonyl Anthrose-β-Tetra | C1 | 6.21 | 0.17 |
| 20 | 5-Methoxycarbonyl β-RhaRhaRha | C2 | 1.04 | 0.05 |
| 17 | 5-Methoxycarbonyl α-RhaRhaRha | C3 | 1.00 | 0.03 |
| 1 | 5-Methoxycarbonyl Anthrose | C4 | 1.15 | 0.01 |
| 35 | Pn23 polysaccharide | C5 | 36.14 | 4.17 |
| | Subarray-d, IgG 20 μg/ml: | 5-Methoxycarbonyl Anthrose-α-Di 0.25 mg/ml | | |
| 34 | Isolichenin | A1 | 11.72 | 3.67 |
| 21 | Me α-L-RhaGal | A2 | 0.98 | 0.03 |
| 24 | Me L-α-Rha((1→3)Rha | A3 | 0.99 | 0.06 |
| 25 | Me α-L-RhaRhaGal | A4 | 0.98 | 0.04 |
| 22 | Me α-D-GlcNAcRhaRhaGal | A5 | 0.98 | 0.01 |
| 3 | 5-Methoxycarbonyl Anthrose-α-Tri | B1 | 0.95 | 0.02 |
| 14 | 5-Methoxycarbonyl α-L-Rha | B2 | 0.94 | 0.04 |
| 16 | 5-Methoxycarbonyl αRha(1→3)Rha | B3 | 1.04 | 0.10 |
| 5 | 5-Methoxycarbonyl Anthrose-α-Tetra | B4 | 0.94 | 0.02 |
| 15 | 5-Methoxycarbonyl β-L-Rha | B5 | 0.98 | 0.03 |
| 4 | 5-Methoxycarbonyl Anthrose-β-Tetra | C1 | 0.93 | 0.04 |
| 20 | 5-Methoxycarbonyl β-RhaRhaRha | C2 | 0.94 | 0.03 |
| 17 | 5-Methoxycarbonyl α-RhaRhaRha | C3 | 0.99 | 0.01 |
| 1 | 5-Methoxycarbonyl Anthrose | C4 | 0.99 | 0.04 |
| 35 | Pn23 polysaccharide | C5 | 26.34 | 3.18 |
| | Subarray-e, IgG 20 μg/ml: | 5-Methoxycarbonyl Anthrose-α-Tetra 0.25 mg/ml | | |
| 34 | Isolichenin | A1 | 30.65 | 1.07 |
| 21 | Me α-L-RhaGal | A2 | 1.09 | 0.06 |
| 24 | Me L-α-Rha((1→3)Rha | A3 | 0.98 | 0.08 |
| 25 | Me α-L-RhaRhaGal | A4 | 1.01 | 0.02 |
| 22 | Me α-D-GlcNAcRhaRhaGal | A5 | 1.01 | 0.04 |
| 3 | 5-Methoxycarbonyl Anthrose-α-Tri | B1 | 0.96 | 0.02 |
| 14 | 5-Methoxycarbonyl α-L-Rha | B2 | 0.99 | 0.04 |
| 16 | 5-Methoxycarbonyl αRha(1→3)Rha | B3 | 0.95 | 0.04 |
| 5 | 5-Methoxycarbonyl Anthrose-α-Tetra | B4 | 0.98 | 0.02 |
| 15 | 5-Methoxycarbonyl β-L-Rha | B5 | 1.00 | 0.03 |
| 4 | 5-Methoxycarbonyl Anthrose-β-Tetra | C1 | 1.01 | 0.03 |
| 20 | 5-Methoxycarbonyl β-RhaRhaRha | C2 | 0.99 | 0.06 |
| 17 | 5-Methoxycarbonyl α-RhaRhaRha | C3 | 0.99 | 0.05 |
| 1 | 5-Methoxycarbonyl Anthrose | C4 | 0.97 | 0.03 |
| 35 | Pn23 polysaccharide | C5 | 18.50 | 1.48 |
| | Subarray-f, IgG 10 μg/ml: | 5-Methoxycarbonyl Anthrose-β-Tetra 0.25 mg/ml | | |
| 34 | Isolichenin | A1 | 10.40 | 0.43 |
| 21 | Me α-L-RhaGal | A2 | 1.09 | 0.02 |
| 24 | Me L-α-Rha((1→3)Rha | A3 | 1.05 | 0.04 |
| 25 | Me α-L-RhaRhaGal | A4 | 1.08 | 0.03 |
| 22 | Me α-D-GlcNAcRhaRhaGal | A5 | 1.05 | 0.01 |
| 3 | 5-Methoxycarbonyl Anthrose-α-Tri | B1 | 1.07 | 0.04 |
| 14 | 5-Methoxycarbonyl α-L-Rha | B2 | 0.98 | 0.01 |
| 16 | 5-Methoxycarbonyl αRha(1→3)Rha | B3 | 1.03 | 0.01 |
| 5 | 5-Methoxycarbonyl Anthrose-α-Tetra | B4 | 1.07 | 0.03 |
| 15 | 5-Methoxycarbonyl β-L-Rha | B5 | 1.06 | 0.05 |
| 4 | 5-Methoxycarbonyl Anthrose-β-Tetra | C1 | 1.04 | 0.06 |
| 20 | 5-Methoxycarbonyl β-RhaRhaRha | C2 | 1.06 | 0.05 |
| 17 | 5-Methoxycarbonyl α-RhaRhaRha | C3 | 1.04 | 0.02 |
| 1 | 5-Methoxycarbonyl Anthrose | C4 | 1.02 | 0.04 |
| 35 | Pn23 polysaccharide | C5 | 15.12 | 0.39 |
| 34 | Isolichenin | A1 | 10.40 | 0.43 |

*IgG signal is measured as the ratio of the mean fluorescent intensity of triplicate detections over the mean intensity of 112 blank spots chosen from within the same subarray.

**See Table 1 for structural information for the compounds whose short names are disclosed in Table 2.

Instrumental Measurements

UV-vis spectra were obtained using a Shimadzu (UV-2401PC) UV-vis recording spectrophotometer. Contact angle measurements were performed with a Rame-Hart 100-00 contact angle goniometer using Millipore Mili-Q water. At least three droplets were measured on each sample and averaged. Thicknesses were measured with a Beaglehole ellipsometer in variable angle mode. A refractive index of 1.5 was used for all samples. Measurements were performed three times in different locations on the surface and averaged. Fluorescence spectra were obtained using a Jobin Yvon Fluorolog 3 spectrofluorimeter in front face mode. The surface was placed at an angle of 20° to a line parallel to the plane of the detector.

The above exemplary method to make a carbohydrate microarray has been repeated using the photoactive benzophenone compound II-1 in place of the photoactive phthalimide compound I-1.

Figure 3A:
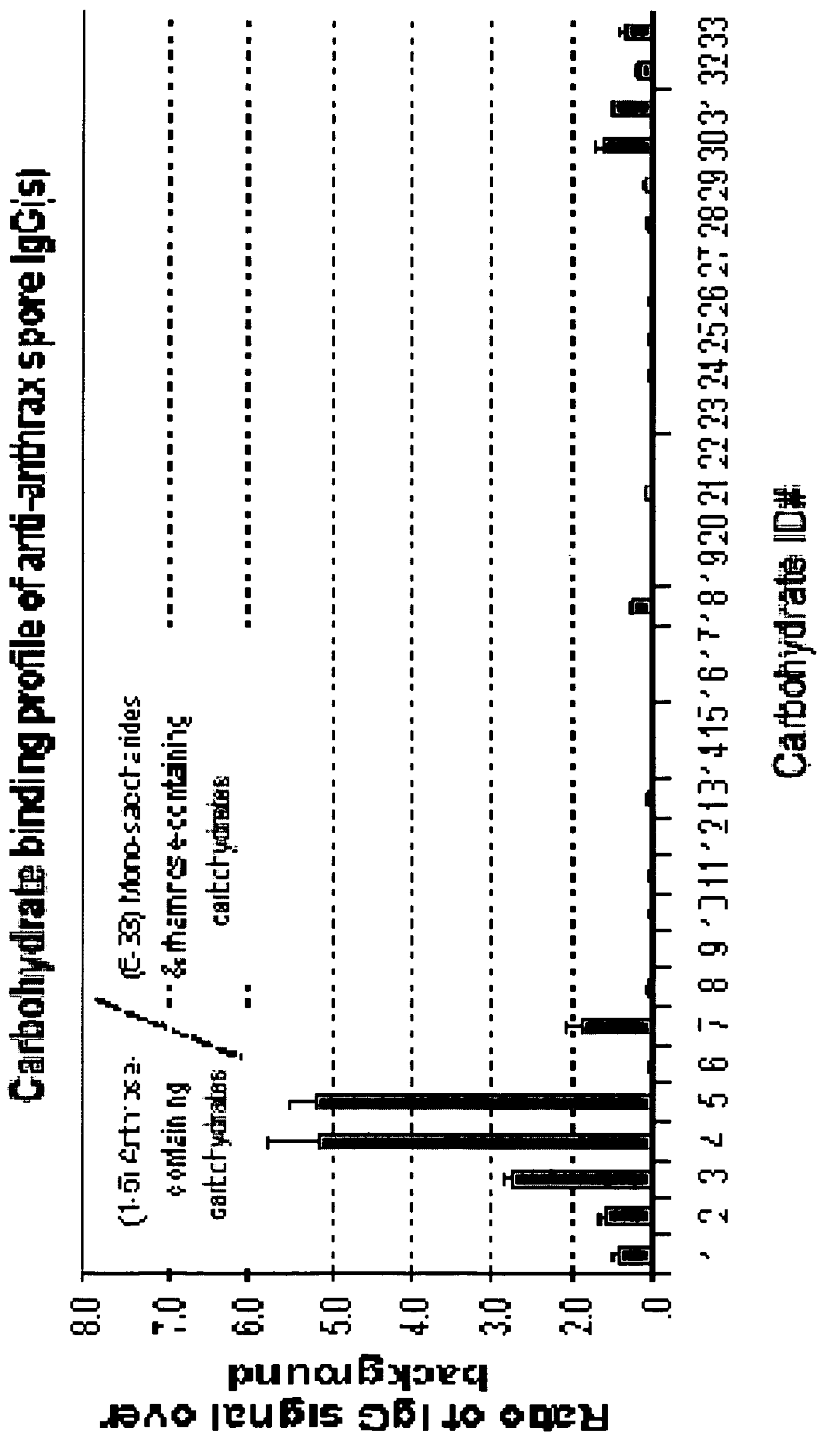
FIG. 3A depicts histograms of the fluorescent signal-to-background ratio for binding of a preparation of rabbit anti-*B. anthracis* spore polyclonal antibodies to a carbohydrate array of the invention.
Figure 3B:
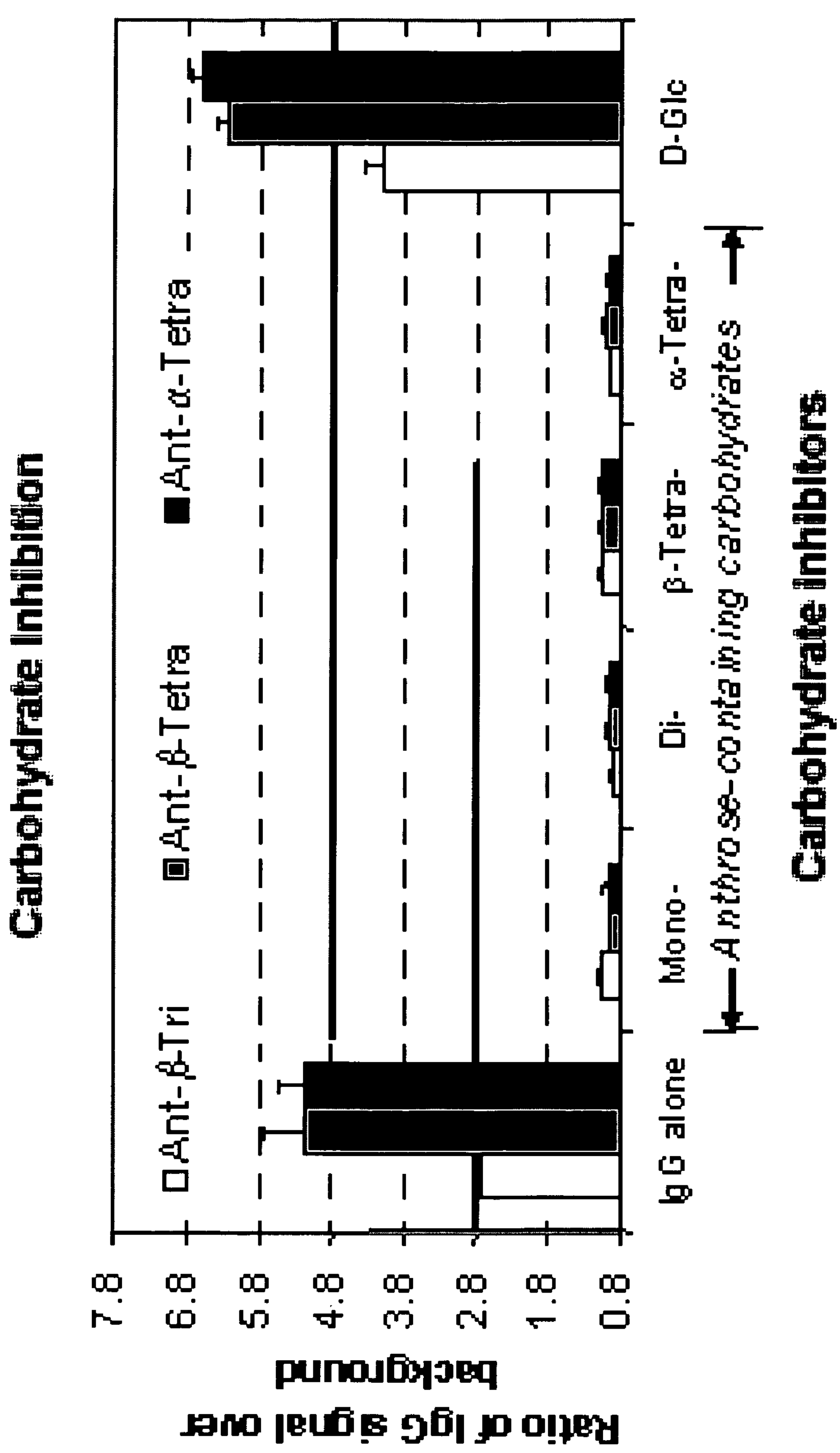
FIG. 3B depicts the results of carbohydrate inhibition on antibody binding to a carbohydrate array of the invention.
Figure 3C:
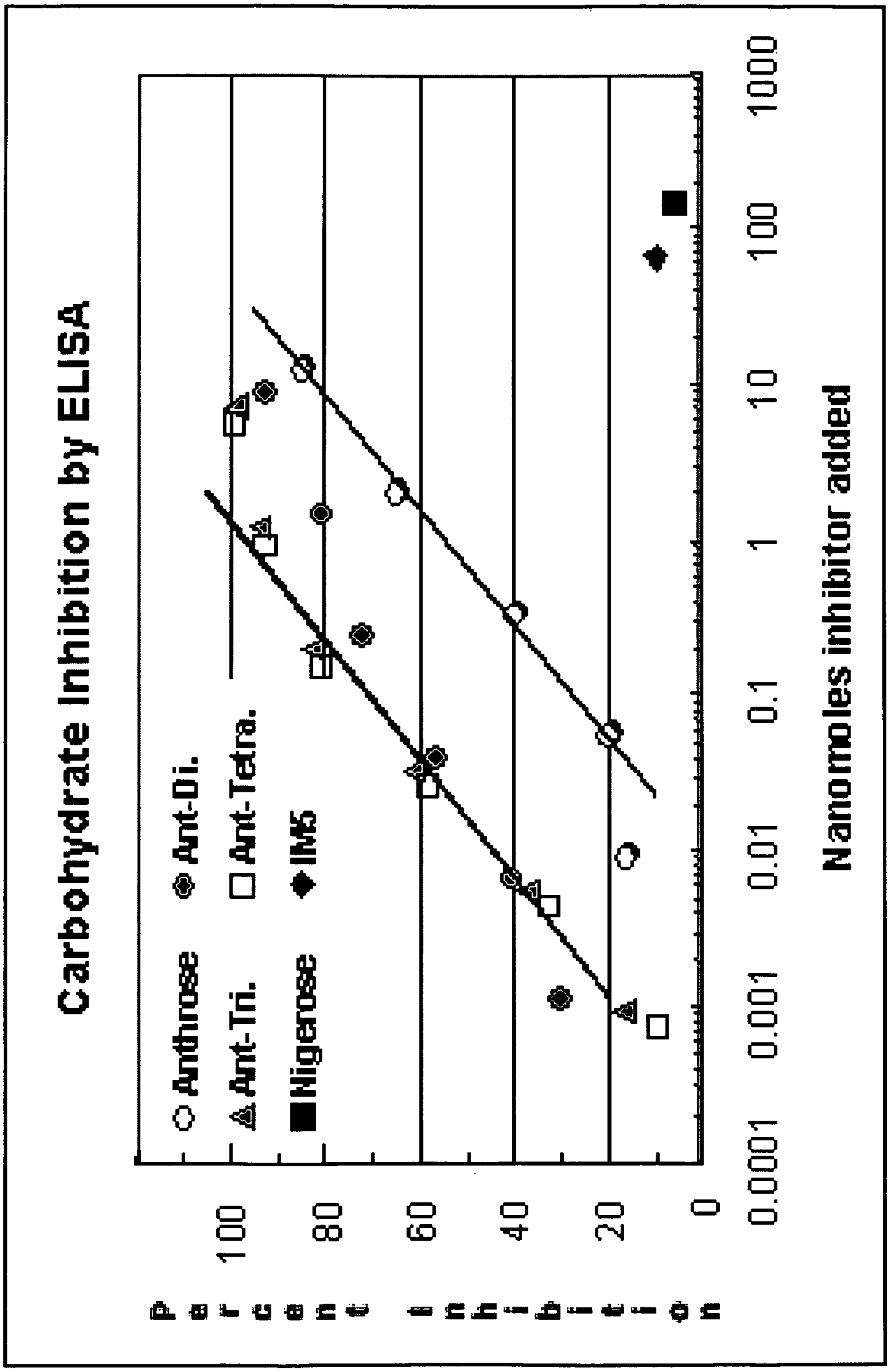
FIG. 3C depicts ELISA-based quantitative carbohydrate inhibition assays.

FIG. 3 depicts quantitative results from screening a photogenerated carbohydrate array of the invention. The carbohydrate epitopes of anti-*B. anthracis* antibodies were mapped using carbohydrate inhibition assays to identify the key elements of several anthrose-containing antigenic carbohydrates. The data used to generate FIG. 3A-C are given in Table 3, below, which includes carbohydrate array characterization data using rabbit polyclonal antibodies elicited by immunization with *B. anthracis* spores.

FIG. 3A depicts histograms of the fluorescent signal-to-background ratio for binding of a preparation of rabbit anti-*B. anthracis* spore polyclonal antibodies to an exemplary carbohydrate microarray of the invention. The levels of IgG antibody reactivity are depicted as the ratios of the mean values of fluorescence intensity over the background, where the background is the mean value of 112 blank spots chosen from within the same carbohydrate array. Each histogram reflects the mean intensity of triplicate spots of the listed carbohydrate. Carbohydrate Id#: 1) anthrose monosaccharide; 2) anthrose-containing disaccharide; 3) anthrose-containing trisaccharide; 4) anthrose-containing β-tetrasaccharide; 5) anthrose-containing α-tetrasaccharide; 6-33) carbohydrates without anthrose, including monosaccharides and a panel of rhamnose-containing oligosaccharides (See Table 1 for structural information and Table 3 for data).

FIG. 3B depicts the results of carbohydrate inhibition on antibody binding to a carbohydrate array of the invention. The results are illustrated as the level of fluorescent signal from carbohydrate-specific IgG antibodies captured by the carbohydrate array in the presence or absence of a carbohydrate inhibitor. Each histogram represents the mean value of a specific antibody's binding to a carbohydrate arrayed in triplicate. For each candidate carbohydrate listed, at least two array assays were conducted to determine the inhibitory activity.

FIG. 3C depicts enzyme-linked immunosorbent assay (ELISA) based quantitative carbohydrate inhibition assays. ELISA microtiter plates (NUNC, MaxiSorp) were coated with a bovine serum albumin (BSA) conjugate of α-anthrose-tetrasaccharide at 5 μg/ml in 0.1M sodium bicarbonate buffer, pH 9.6, and were incubated with a preparation of rabbit anti-*B. anthracis* spore IgG (2 μg/ml) in the presence or absence of varying quantities of the carbohydrate inhibitors. The half maximal inhibitory concentration ($IC_{50}$) values for given carbohydrates were calculated based on mathematical models of the linear range of the corresponding carbohydrate inhibition curve. Percent inhibition was calculated as follows: % inhibition=((standard A−blank A)−(A with inhibitor−blank A))/(standard A−blank A).

TABLE 3

| Saccharide arrays | | *IgG signal detected by carbohydrate arrays (n = 3) | |
|---|---|---|---|
| Id# | **Short name | Mean | SD |
| 1 | 5-Methoxycarbonyl Anthrose | 1.44 | 0.08 |
| 2 | 5-Methoxycarbonyl Anthrose-α-Di | 1.65 | 0.06 |
| 3 | 5-Methoxycarbonyl Anthrose-α-Tri | 2.73 | 0.09 |
| 4 | 5-Methoxycarbonyl Anthrose-β-Tetra | 5.16 | 0.58 |
| 5 | 5-Methoxycarbonyl Anthrose-α-Tetra | 5.19 | 0.31 |
| 6 | L-Rha | 1.03 | 0.05 |
| 7 | D-Fuc | 1.88 | 0.21 |
| 8 | D-Gal | 1.06 | 0.05 |
| 9 | D-Glc | 1.04 | 0.00 |
| 10 | D-Man | 1.03 | 0.01 |
| 11 | GalNAc | 1.03 | 0.01 |
| 12 | L-Ara | 1.03 | 0.01 |
| 13 | L-Man | 1.06 | 0.04 |
| 14 | 5-Methoxycarbonyl α-L-Rha | 0.97 | 0.03 |
| 15 | 5-Methoxycarbonyl β-L-Rha | 0.95 | 0.01 |
| 16 | 5-Methoxycarbonyl α-Rha(1→3)Rha | 1.00 | 0.04 |
| 17 | 5-Methoxycarbonyl α-RhaRhaRha | 0.98 | 0.01 |
| 18 | 5-Methoxycarbonyl αRha(1→2)Rha | 1.26 | 0.07 |
| 19 | 5-Methoxycarbonyl βRha(1→2)Rha | 0.98 | 0.03 |
| 20 | 5-Methoxycarbonyl β-RhaRhaRha | 0.95 | 0.04 |
| 21 | Me α-L-RhaGal | 1.08 | 0.05 |
| 22 | Me α-D-GlcNAcRhaRhaGal | 0.95 | 0.03 |
| 23 | Me α-L-RhaGalGlcNAc | 1.01 | 0.02 |
| 24 | Me L-α-Rha(1→3)Rha | 1.02 | 0.04 |
| 25 | Me α-L-RhaRhaGal | 1.02 | 0.04 |
| 26 | Me α-L-RhaGalGlcNAc | 1.01 | 0.04 |
| 27 | Ogawa-Tri | 1.01 | 0.02 |
| 28 | Ogawa-Tetra | 1.07 | 0.02 |
| 29 | Ogawa-Penta | 1.09 | 0.06 |
| 30 | Ogawa-Hexa | 1.67 | 0.09 |
| 31 | Ogawa-Tri-BSA | 1.53 | 0.02 |
| 32 | Ogawa-Tetra-BSA | 1.20 | 0.04 |
| 33 | Ogawa-Penta-BSA | 1.37 | 0.05 |

*IgG signal is measured as the ratio of the mean fluorescent intensity of triplicate detections over the mean intensity of 112 blank spots chosen from within the same subarray.
**See Table 1 for structural information for the compounds whose short names are disclosed in Table 3.

The following documents are hereby incorporated by reference in their entireties.

Pirrung, M. C. How to make a DNA chip. *Angewandte Chemie, International Edition* 41, 1276-1289 (2002).

Blawas, A. S. & Reichert, W. M. Protein patterning. *Biomaterials* 19, 595-609 (1998).

Whitesides, G. M., Ostuni, E., Takayama, S., Jiang, X. & Ingber, D. E. Soft lithography in biology and biochemistry. *Annu. Rev. Biomed. Eng.* 3, 335-373 (2001).

Chen, C. S., Mrksich, M., Huang, S., Whitesides, G. M. & Ingber, D. E. Geometric control of cell life and death. *Science* 276, 1425-1428 (1997).

Liu, G.-Y. & Amro, N. A. Positioning protein molecules on surfaces: a nanoengineering approach to supramolecular chemistry. *Proc. Natl. Acad. Sci. U.S.A.* 99, 5165-5170 (2002).

Langer, R. & Vacanti, J. P. Tissue engineering. *Science* 260, 920-926 (1993).

Yeong, W.-Y., Chua, C.-K., Leong, K.-F. & Chandrasekaran, M. Rapid prototyping in tissue engineering: challenges and potential. *Trends Biotechnol.* 22, 643-652 (2004).

Jelinek, R. & Kolusheva, S. Carbohydrate Biosensors. *Chem. Rev.* 104, 5987-6015 (2004).

Fukui, S., Feizi, T., Galustian, C., Lawson Alexander, M. & Chai, W. Oligosaccharide microarrays for high-throughput detection and specificity assignments of carbohydrate-protein interactions. *Nature Biotechnol.* 20, 1011-1017 (2002).

Fazio, F., Bryan, M. C., Blixt, O., Paulson, J. C. & Wong, C.-H. Synthesis of Sugar Arrays in Microtiter Plate. *J. Am. Chem. Soc.* 124, 14397-14402 (2002).

Bryan, M. C., Lee, L. V. & Wong, C.-H. High-throughput identification of fucosyltransferase inhibitors using carbohydrate microarrays. *Bioorg. Med. Chem. Lett.* 14, 3185-3188 (2004).

Disney Matthew, D. & Seeberger Peter, H. The use of carbohydrate microarrays to study carbohydrate-cell interactions and to detect pathogens. *Chem. Biol.* 11, 1701-1707 (2004).

Nimrichter, L. et al. Intact cell adhesion to glycan microarrays. *Glycobiology* 14, 197-203 (2004).

Wang, D., Liu, S., Trummer, B. J., Deng, C. & Wang, A. Carbohydrate microarrays for the recognition of cross-reactive molecular markers of microbes and host cells. *Nature Biotechnol.* 20, 275-281 (2002).

Park, S., Lee, M.-R., Pyo, S.-J. & Shin, I. Carbohydrate chips for studying high-throughput carbohydrate-protein interactions. *J. Am. Chem. Soc.* 126, 4812-4819 (2004).

Park, S. & Shin, I. Fabrication of carbohydrate chips for studying protein-carbohydrate interactions. *Angew. Chem., Int. Ed. Engl.* 41, 3180-3182 (2002).

Shin, I., Park, S. & Lee, M.-r. Carbohydrate microarrays: An advanced technology for functional studies of glycans. *Chem. Eur.* 111, 2894-2901 (2005).

Takahashi, S. & Anzai, J. Phenylboronic acid monolayer-modified electrodes sensitive to sugars. *Langmuir* 21, 5102-5107 (2005).

Angeloni, S. et al. Glycoprofiling with micro-arrays of glycoconjugates and lectins. *Glycobiology* 15, 31-41 (2005).

De Smet, L. C. P. M. et al. Covalently attached saccharides on silicon surfaces. *J. Am. Chem. Soc.* 125, 13916-13917 (2003).

Fodor, S. P. A. et al. Light-directed, spatially addressable parallel chemical synthesis. *Science* 251, 767-773 (1991).

Rozsnyai, L. F., Fodor, S. P. A., Schultz, P. G. & Benson, D. R. Photolithographic immobilization of biopolymers on solid supports. *Angew. Chem.* 104, 801-802 (See also Angew Chem, Int Ed Engl, 1992, 1931 (1996), 1759-1961) (1992).

Lee, K., Pan, F., Carroll, G. T., Turro, N. J. & Koberstein, J. T. Photolithographic Technique for Direct Photochemical Modification and Chemical Micropatterning of Surfaces. *Langmuir* 20, 1812-1818 (2004).

Husemann, M. et al. Manipulation of Surface Properties by Patterning of Covalently Bound Polymer Brushes. *J. Am. Chem. Soc.* 122, 1844-1845 (2000).

Turro, N. J. Modern Molecular Photochemistry. (University Science Books, Sausalito, Calif.; 1991).

Kanaoka, Y. Photoreactions of cyclic imides. Examples of synthetic organic photochemistry. *Acc. Chem. Res.* 11, 407-413 (1978).

Moon, J. H., Shin, J. W., Kim, S. Y. & Park, J. W. Formation of Uniform Aminosilane Thin Layers: An Imine Formation To Measure Relative Surface Density of the Amine Group. *Langmuir* 12, 4621-4624 (1996).

Prucker, O., Naumann, C. A., Ruehe, J., Knoll, W. & Frank, C. W. Photochemical Attachment of Polymer Films to Solid Surfaces via Monolayers of Benzophenone Derivatives. *J. Am. Chem. Soc.* 121, 8766-8770 (1999).

Lopez, G. P., Biebuyck, H. A., Frisbie, C. D. & Whitesides, G. M. Imaging of features on surfaces by condensation figures. *Science* 260, 647-649 (1993).

Willats William, G. T., Rasmussen Svend, E., Kristensen, T., Mikkelsen Jorn, D. & Knox, J. P. Sugar-coated microarrays: a novel slide surface for the high-throughput analysis of glycans. *Proteomics* 2, 1666-1671 (2002).

Mock, M., Fouet, A., *Annu Rev Microbiol* 2001, 55, 647-671.

Webb, G. F., *Proc Natl Acad Sci USA* 2003, 100, 4355-4356.

Newcombe, D. A., Schuerger, A. C., Benardini, J. N., Dickinson, D., et al., *Appl Environ Microbiol* 2005, 71, 8147-8156.

Williams, D. D., Benedek, O., Turnbough, C. L., Jr., *Appl Environ Microbiol* 2003, 69, 6288-6293.

Turnbull, P. C. B., *Curr. Opin. Infect. Dis.* 2000, 13, 113-120.

Cohen, S., Mendelson, I., Altboum, Z., Kobiler, D., et al., *Infect Immun* 2000, 68, 4549-4558.

Kramer, M. J., Roth, I. L., *Can J Microbiol* 1968, 14, 1297-1299.

Kramer, M. J., Roth, I. L., *Can J Microbiol* 1969, 15, 1247-1248.

Lai, E. M., Phadke, N. D., Kachman, M. T., Giomo, R., et al., *J Bacteriol* 2003, 185, 1443-1454.

Redmond, C., Baillie, L. W., Hibbs, S., Moir, A. J., Moir, A., *Microbiology* 2004, 150, 355-363.

Sylvestre, P., Couture-Tosi, E., Mock, M., *Mol Microbiol* 2002, 45, 169-178.

Daubenspeck, J. M., Zeng, H., Chen, P., Dong, S., et al., *J Biol Chem* 2004, 279, 30945-30953.

Steichen, C., Chen, P., Kearney, J. F., Turnbough, C. L., Jr., *J Bacteriol* 2003, 185, 1903-1910.

Boydston, J. A., Chen, P., Steichen, C. T., Turnbough, C. L., Jr., *J Bacteriol* 2005, 187, 5310-5317.

Carroll, G. T., Wang, D., Turro, N. J., Koberstein, J. T., *Langmuir* 2006, 22, 2899-2905.

Zhang, J., Kovac, P., *Carbohydr Res* 1997, 300, 329-339.

Cisar, J., Kabat, E. A., Domer, M. M., Liao, J., *J. Exp. Med.* 1975, 142, 435-459.

Kovac, P., Lerner, L., *Carbohydr Res* 1988, 184, 87-112.

Wang, D., Liu, S., Trummer, B. J., Deng, C., Wang, A., *Nat Biotechnol* 2002, 20, 275-281.

Saksena, R., Adamo, R., Kovac, P., *Carbohydr Res* 2005, 340, 1591-1600.

Saksena, R., Adamo, R., Kovac, P., *Bioorg Med Chem Lett* 2006, 16, 615-617.

Adamo, R., Saksena, R., Kovac, P., *Carbohydr Res* 2005, 340, 2579-2582.

Wang, D., Lu, J., *Physiol Genomics* 2004, 18, 245-248.

Wang, R., Liu, S., Shah, D., Wang, D., *Methods Mol Biol* 2005, 310, 241-252.

Wang, D., *Proteomics* 2003, 3, 2167-2175.

Saksena, R. et al., Carbohydr Res 340, 1591-1600 (2005).

Adamo, R. et al., Carbohydr Res 340, 2579-2582 (2005);

Saksena, R. et al., Bioorg Med Chem Lett 16, 615-617 (2006).

Kovácv et. al. J. Org. Chem., 57, 2455-2467 (1992).

Pavliak et. al., Carbohydr. Res., 229, 103-116 (1992).

Zhang, J. & Kovac, P., Carbohydr. Res 300, 329-339 (1997)

Saksena et. al., Carbohydr. Res., 338, 2591-2603 (2003).

Heidelberger M., J. Immunol.; 91:735-9, (1963)

Roy, A. & Roy, N., Carbohydrate Res., 126:271-7, (1984); Heidelberger M. et al., J. Immunol. 99:794-6, (1967).

As various changes can be made in the above methods and compositions without departing from the scope and spirit of the invention as described, it is intended that all subject matter contained in the above description, shown in the accompanying drawings, or defined in the appended claims be interpreted as illustrative and not limiting.

What is claimed is:

1. A microarray comprising:

a surface;

a compound of formula (I):

(I)

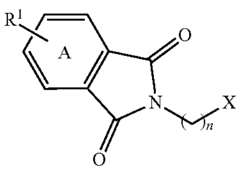

immobilized on at least a part of the surface;

one or more carbohydrates attached to the surface through a covalent bond to the compound of formula (I), wherein the covalent bond is photochemically generated;

a compound of Formula (III) immobilized on the surface:

(III)

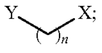

wherein the compound of formula (I) and the compound of formula (III) are mixed in the microarray; and wherein one or more of the carbohydrates are capable of binding to an agent, wherein the agent is capable of indicating a presence of a disease or a pathogen;

n is an integer from 1 to 100;

X is $R^2$, —$CO_2R^3$, —C(O)$NR^3R^3$, —$SR^4$, —CN, —$OR^3$, a halogen, a β-diketone, a silane, a phosphate, a phosphonate, a polymer, or block copolymer;

ring A is substituted with one or more $R_1$ groups;

$R_1$ is independently a halogen, a hydroxyl, an aryl, an amide, a cyano, a nitro, —$R^2$, —C(O)$R^3$, —$CO_2R^3$, —OC(O)$R^3$, or —$OR^3$;

$R^2$ is independently a hydrogen, a substituted or unsubstituted straight- or branched-chain alkyl which contains 1-6 carbons, a substituted or unsubstituted alkene which contains 2-4 carbons, a substituted or unsubstituted alkyne which contains 2-4 carbons, or —OC(O)$R^5$;

$R^3$ is independently a hydrogen, a substituted or unsubstituted $C_1$-$C_{10}$ straight-chain or branched-chain alkyl, or a substituted or unsubstituted alkene which contains 2-4 carbons;

$R^4$ is independently a hydrogen, —S-pyridyl, —$SR^3$, —$SO_2R^3$, or $SR^8$, wherein —$SR^8$ and the rest of formula (I) combine to form a bis-disulfide;

$R^5$ is independently a hydrogen, an unsubstituted straight- or branched-chain alkyl that contains 1-6 carbons, or a straight- or branched-chain alkyl that contains 1-6 carbons and is substituted by an alkyne; and Y is —$NR^3R^3$, —OH, —SH, —C(O)$NR^3R^3$, —$CO_2H$, an ammonium, or a salt thereof.

2. The microarray of claim 1, wherein the agent is a biomarker for a disease.

3. The microarray of claim 1, wherein the agent is an antibody.

4. The microarray of claim 3, wherein the antibody is capable of binding to a specific pathogen.

5. The microarray of claim 4, wherein the pathogen is *Bacillus anthracis*.

6. The microarray of claim 1, wherein n is an integer from 1 to 20.

7. The microarray of claim 1, wherein the compound of Formula (I) is

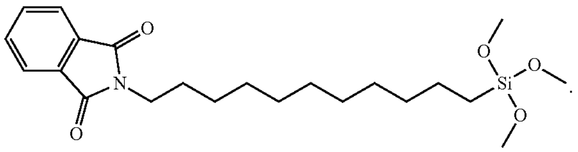 [SMILES: CO[Si](CCCCCCCCCCCN1C(=O)c2ccccc2C1=O)(OC)OC]

8. The microarray of claim 1, wherein at least one carbohydrate is selected from the group consisting of:

2-O-methyl-4-(3-hydroxy-3-methylbutamido)-4,6-dideoxy-D-glucose;

2-O-methyl-4-(3-hydroxy-3-methylbutamido)-4,6-dideoxy-β-D-glucose;

2-O-methyl-4-(3-hydroxy-3-methylbutamido)-4,6-dideoxy-α-D-glucose;

2-O-methyl-4-(3-hydroxy-3-methylbutamido)-4,6-dideoxy-β-D-glucopyranosyl-(1→3)-α-L-rhamnopyranose;

2-O-methyl-4-(3-hydroxy-3-methylbutamido)-4,6-dideoxy-β-D-glucopyranosyl-(1→3)-β-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranose;

α-L-rhamnopyranosyl-(1→3)-α-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-β-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-α-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-β-L-rhamnopyranose;

α-L-rhamnopyranosyl-(1→3)-α-L-rhamnopyranosyl-(1→2)-L-rhamnopyranose;

α-L-rhamnopyranosyl-(1→3)-α-L-rhamnopyranosyl-(1→2)-β-L-rhamnopyranose;

α-L-rhamnopyranosyl-(1→3)-α-L-rhamnopyranosyl-(1→2)-α-L-rhamnopyranose;

5-(Methoxycarbonyl)-pentyl-4-(3-hydroxy-3-methylbutanamido)-2-O-methyl-4,6-dideoxy-α-D-glucopyranoside;

5-(Methoxycarbonyl)-pentyl-4-(3-hydroxy-3-methylbutanamido)-2-O-methyl-4,6-dideoxy-α-D-glucopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranosyl-(1→2)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranosyl-(1→2)-β-L-rhamnopyranoside;

n-Pentenyl 4,6-Dideoxy-4-(3-hydroxy-3-methylbutanamido)-2-O-methyl-β-D-glucopyranose;

n-Pentenyl 4,6-Dideoxy-4-(3-hydroxy-3-methylbutanamido)-2-O-methyl-β-Dglucopyranosyl-(1→3)-α-L-rhamnopyranose;

n-Pentenyl 4,6-Dideoxy-4-(3-hydroxy-3-methylbutanamido)-2-O-methyl-β-D-glucopyranosyl-(1→3)-β-L-rhamnopyranose;

n-Pentenyl 4,6-Dideoxy-4-(3-hydroxy-3-methylbutanamido)-2-O-methyl-β-D-glucopyranosyl-(1→3)-α-L-rhamnopyranosyl-(1→3)-α-L-rhamnopyranose;

n-Pentenyl 4,6-Dideoxy-4-(3-hydroxy-3-methylbutanamido)-2-O-methyl-β-D-glucopyranosyl-(1→3)-β-L-rhamnopyranosyl-(1→3)-α-L-rhamnopyranose;

L-rhamnopyranosyl-(1→3)-α-L-rhamnopyranosyl-(1→2)-α-L-rhamnopyranose;

n-Pentenyl 4,6-Dideoxy-4-(3-hydroxy-3-methylbutanamido)-2-O-methyl-β-Dglucopyranosyl-(1→3)-α-L-rhamnopyranosyl-(1→3)-α-L-rhamnopyranosyl-(1→2)-α-L-rhamnopyranose; or n-Pentenyl 4,6-Dideoxy-4-(3-hydroxy-3-methylbutanamido)-2-O-methyl-β-Dglucopyranosyl-(1→3)-β-L-rhamnopyranosyl-(1→3)-α-L-rhamnopyranosyl-(1→2)-α-L-rhamnopyranose, 5-(Methoxycarbonyl)-pentyl-4-(3-hydroxy-3-methylbutanamido)-2-O-methyl-4,6-dideoxy-β-D-glucopyranosyl-(1→3)-α-L-rhamnopyranosyl-(1→3)-α-L-rhamnopyranosyl-(1→2)-β-L-rhamnopyranose;

Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-tetrakis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

[Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside]$_5$-BSA;

[Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA;

[Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA;

glycosides thereof; and combinations thereof.

9. The microarray of claim 1, wherein the compound of formula (I) forms a self-assembled monolayer.

10. The microarray of claim 1, wherein Y is —$NH_2$.

11. The microarray of claim 10, wherein the compound of Formula (III) and the compound of Formula (I) are present in a ratio from about 1:1 to about 100:1.

12. The microarray of claim 11, wherein the ratio is from about 5:1 to about 20:1.

13. The microarray of claim 1, wherein the compound of Formula (III) is

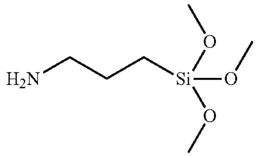

.

14. The microarray of claim 1, wherein the array comprises a chip, a plate, a sensor, a slide, a combination thereof, or a portion thereof.

15. The microarray of claim 1, wherein the surface comprises an inorganic material.

16. The microarray of claim 15, wherein the surface comprises silica, glass, quartz, silicon, titanium, titania, gold, or a combination thereof.

17. The microarray of claim 1, wherein the surface comprises an organic material.

18. The microarray of claim 17, wherein the surface comprises polyacrylamide, nylon, polyethylene, polypropylene, PTFE, polycarbonate, polystyrene, poly(tert-butyl acrylate), poly(vinyl alcohol), nitrocellulose, or a combination thereof.

19. The microarray of claim 1, wherein the compound of Formula (III) is

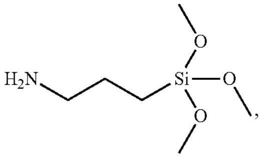

,

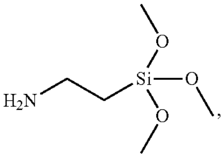

,

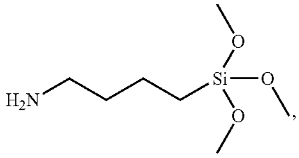

,

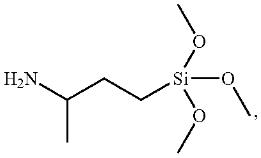

,

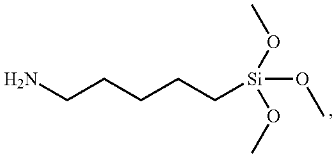

, or

-continued

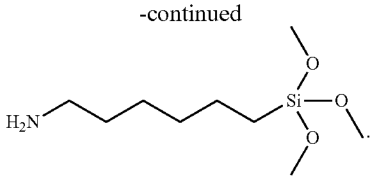

20. The microarray of claim 1, wherein the compound of Formula (I) is

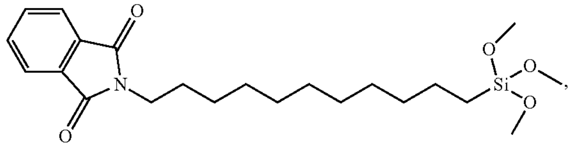,

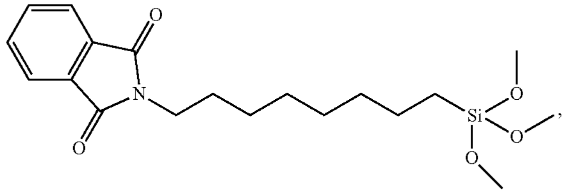,

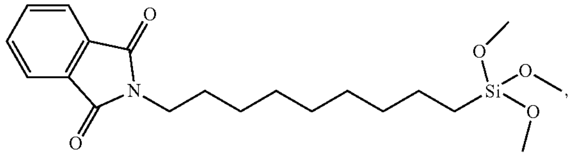,

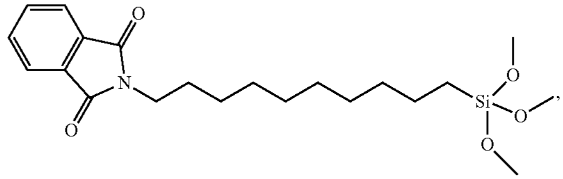,

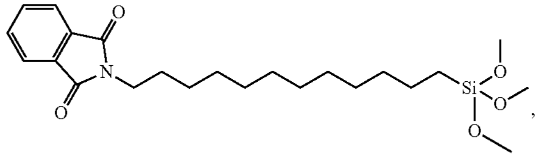, or

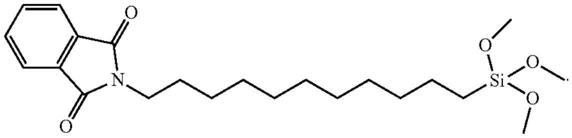.

21. The microarray of claim 1, wherein the compound of Formula (I) is

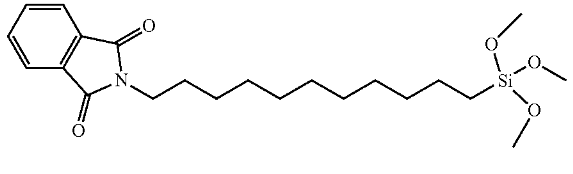 [SMILES: CO[Si](CCCCCCCCCCCN1C(=O)c2ccccc2C1=O)(OC)OC]

and the compound of Formula (III) is

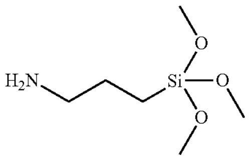.

22. The microarray of claim 21, wherein at least one carbohydrate is selected from the group consisting of:

2-O-methyl-4-(3-hydroxy-3-methylbutamido)-4,6-dideoxy-D-glucose;

2-O-methyl-4-(3-hydroxy-3-methylbutamido)-4,6-dideoxy-β-D-glucose;

2-O-methyl-4-(3-hydroxy-3-methylbutamido)-4,6-dideoxy-α-D-glucose;

2-O-methyl-4-(3-hydroxy-3-methylbutamido)-4,6-dideoxy-β-D-glucopyranosyl-(1→3)-α-L-rhamnopyranose;

2-O-methyl-4-(3-hydroxy-3-methylbutamido)-4,6-dideoxy-β-D-glucopyranosyl-(1→3)-β-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranose;

α-L-rhamnopyranosyl-(1→3)-α-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-β-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-α-L-rhamnopyranose;

2-O-methyl-4-(3-hydroxy-3-methylbutamido)-4,6-dideoxy-β-D-glucopyranosyl-(1→3)-α-L-rhamnopyranosyl-(1→3)-α-L-rhamnopyranosyl-(1→2)-β-L-rhamnopyranose;

α-L-rhamnopyranosyl-(1→3)-α-L-rhamnopyranosyl-(1→2)-L-rhamnopyranose;

α-L-rhamnopyranosyl-(1→3)-α-L-rhamnopyranosyl-(1→2)-β-L-rhamnopyranose;

α-L-rhamnopyranosyl-(1→3)-α-L-rhamnopyranosyl-(1→2)-α-L-rhamnopyranose;

5-(Methoxycarbonyl)-pentyl-4-(3-hydroxy-3-methylbutanamido)-2-O-methyl-4,6-dideoxy-α-D-glucopyranoside;

5-(Methoxycarbonyl)-pentyl-4-(3-hydroxy-3-methylbutanamido)-2-O-methyl-4,6-dideoxy-α-D-glucopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranosyl-(1→2)-α-L-rhamnopyranoside;

5-(Methoxycarbonyl)-pentyl-4-(3-hydroxy-3-methylbutanamido)-2-O-methyl-4,6-dideoxy-α-D-glucopyranosyl-(1→3)-α-L-rhamnopyranosyl-(1→3)-α-L-rhamnopyranosyl-(1→2)-β-L-rhamnopyranoside;

n-Pentenyl 4,6-Dideoxy-4-(3-hydroxy-3-methylbutanamido)-2-O-methyl-β-D-glucopyranose;

n-Pentenyl 4,6-Dideoxy-4-(3-hydroxy-3-methylbutanamido)-2-O-methyl-β-Dglucopyranosyl-(1→3)-α-L-rhamnopyranose;

n-Pentenyl 4,6-Dideoxy-4-(3-hydroxy-3-methylbutanamido)-2-O-methyl-β-D-glucopyranosyl-(1→3)-β-L-rhamnopyranose;

n-Pentenyl 4,6-Dideoxy-4-(3-hydroxy-3-methylbutanamido)-2-O-methyl-β-D-glucopyranosyl-(1→3)-α-L-rhamnopyranosyl-(1→3)-α-L-rhamnopyranose;

n-Pentenyl 4,6-Dideoxy-4-(3-hydroxy-3-methylbutanamido)-2-O-methyl-β-D-glucopyranosyl-(1→3)-β-L-rhamnopyranosyl-(1→3)-α-L-rhamnopyranose;

L-rhamnopyranosyl-(1→3)-α-L-rhamnopyranosyl-(1→2)-α-L-rhamnopyranose;

n-Pentenyl 4,6-Dideoxy-4-(3-hydroxy-3-methylbutanamido)-2-O-methyl-β-Dglucopyranosyl-(1→3)-α-L-rhamnopyranosyl-(1→3)-α-L-rhamnopyranosyl-(1→2)-α-L-rhamnopyranose; or n-Pentenyl 4,6-Dideoxy-4-(3-hydroxy-3-methylbutanamido)-2-O-methyl-β-Dglucopyranosyl-(1→3)-β-L-rhamnopyranosyl-(1→3)-α-L-rhamnopyranosyl-(1→2)-α-L-rhamnopyranose, 5-(Methoxycarbonyl)-pentyl-4-(3-hydroxy-3-methylbutanamido)-2-O-methyl-4,6-dideoxy-β-D-glucopyranosyl-(1→3)-α-L-rhamnopyranosyl-(1→3)-α-L-rhamnopyranosyl-(1→2)-β-L-rhamnopyranose;

Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

Methyl 2-O-methyl-4,6-dideoxy-4-(3-deoxy-L-glycero-tetronamido)-D-mannopyranosyl-(1→2)-tetrakis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside;

[Methyl 2-O-methyl-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranosyl-(1→2)-4,6-dideoxy-4-(3-deoxy-L-glycero-tetronamido)-D-mannopyranoside]$_5$-BSA;

[Methyl 2-O-methyl-4,6-dideoxy-4-(3-deoxy-L-glycero-tetronamido)-D-mannopyranosyl-(1→2)-bis[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA;

[Methyl 2-O-methyl-4,6-dideoxy-4-(3-deoxy-L-glycero-tetronamido)-D-mannopyranosyl-(1→2)-tris[4,6-dideoxy-4-(3-deoxy-L-glycero-tetronamido)-D-mannopyranosyl-(1→2)]-4,6-dideoxy-4-(3-deoxy-L-glycero-tetronamido)-D-mannopyranoside]$_{10}$-BSA;

glycosides thereof; and combinations thereof.

* * * * *